(12) United States Patent
Ozcan et al.

(10) Patent No.: US 11,893,739 B2
(45) Date of Patent: *Feb. 6, 2024

(54) METHOD AND SYSTEM FOR DIGITAL STAINING OF LABEL-FREE FLUORESCENCE IMAGES USING DEEP LEARNING

(71) Applicant: THE REGENTS OF THE UNIVERSITY OF CALIFORNIA, Oakland, CA (US)

(72) Inventors: Aydogan Ozcan, Los Angeles, CA (US); Yair Rivenson, Los Angeles, CA (US); Hongda Wang, Los Angeles, CA (US); Zhensong Wei, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 758 days.

This patent is subject to a terminal disclaimer.

(21) Appl. No.: 17/041,447

(22) PCT Filed: Mar. 29, 2019

(86) PCT No.: PCT/US2019/025020
§ 371 (c)(1),
(2) Date: Sep. 25, 2020

(87) PCT Pub. No.: WO2019/191697
PCT Pub. Date: Oct. 3, 2019

(65) Prior Publication Data
US 2021/0043331 A1 Feb. 11, 2021

Related U.S. Application Data

(60) Provisional application No. 62/651,005, filed on Mar. 30, 2018.

(51) Int. Cl.
*G06T 7/11* (2017.01)
*G16H 70/60* (2018.01)
(Continued)

(52) U.S. Cl.
CPC ............ *G06T 7/11* (2017.01); *G06F 18/2155* (2023.01); *G06N 3/08* (2013.01); *G06V 10/764* (2022.01);
(Continued)

(58) Field of Classification Search
CPC ............. G06T 7/11; G06T 2207/10024; G06T 2207/10056; G06T 2207/20081;
(Continued)

(56) References Cited

U.S. PATENT DOCUMENTS 9,971,966 B2   5/2018   Nelson et al.
10,824,847 B2 * 11/2020   Wu ........................ G06T 11/001
(Continued)

FOREIGN PATENT DOCUMENTS

CN   1556379 A    12/2004
CN   102575990 A   7/2012
(Continued)

OTHER PUBLICATIONS

First Examination Report dated Jul. 14, 2022 for Indian Patent Application No. 202037045753, (7 pages).
(Continued)

*Primary Examiner* — Lewis G West
(74) *Attorney, Agent, or Firm* — VISTA IP LAW GROUP LLP

(57) ABSTRACT

A deep learning-based digital staining method and system are disclosed that enables the creation of digitally/virtually-stained microscopic images from label or stain-free samples based on autofluorescence images acquired using a fluorescent microscope. The system and method have particular
(Continued)

applicability for the creation of digitally/virtually-stained whole slide images (WSIs) of unlabeled/unstained tissue samples that are analyzes by a histopathologist. The methods bypass the standard histochemical staining process, saving time and cost. This method is based on deep learning, and uses, in one embodiment, a convolutional neural network trained using a generative adversarial network model to transform fluorescence images of an unlabeled sample into an image that is equivalent to the brightfield image of the chemically stained-version of the same sample. This label-free digital staining method eliminates cumbersome and costly histochemical staining procedures and significantly simplifies tissue preparation in pathology and histology fields.

41 Claims, 10 Drawing Sheets

(51) Int. Cl.
  *G16H 30/20* (2018.01)
  *G16H 30/40* (2018.01)
  *G06N 3/08* (2023.01)
  *G06F 18/214* (2023.01)
  *G06V 10/764* (2022.01)
  *G06V 10/82* (2022.01)

(52) U.S. Cl.
  CPC ............ *G06V 10/82* (2022.01); *G16H 30/20* (2018.01); *G16H 30/40* (2018.01); *G16H 70/60* (2018.01)

(58) Field of Classification Search
  CPC . G06T 2207/20084; G06T 2207/30024; G06F 18/2155; G06F 18/24; G06N 3/08; G06V 10/764; G06V 10/82; G06V 2201/03; G06V 10/10; G16H 30/20; G16H 30/40; G16H 70/60
  See application file for complete search history.

(56) References Cited

U.S. PATENT DOCUMENTS

| | | | |
|---|---|---|---|
| 11,354,804 B1* | 6/2022 | Behrooz | G06N 3/08 |
| 11,403,735 B2* | 8/2022 | Gao | G06T 3/4046 |
| 2004/0093166 A1 | 5/2004 | Kil | |
| 2012/0083678 A1 | 4/2012 | Drauch et al. | |
| 2013/0077875 A1 | 3/2013 | Levenson et al. | |
| 2013/0144714 A1 | 6/2013 | Yuan et al. | |
| 2013/0317369 A1* | 11/2013 | Bryant-Greenwood | A61B 5/0059 382/128 |
| 2014/0221813 A1* | 8/2014 | Bryant-Greenwood | G06T 7/90 600/407 |
| 2014/0270457 A1* | 9/2014 | Bhargava | G06V 20/69 382/133 |
| 2015/0119722 A1* | 4/2015 | Kaneko | A61B 1/043 600/476 |
| 2015/0226743 A1* | 8/2015 | Weiss | G01N 33/57426 424/133.1 |
| 2016/0077007 A1 | 3/2016 | Demos et al. | |
| 2016/0196648 A1* | 7/2016 | Madabhushi | C07K 16/468 382/131 |
| 2017/0052106 A1 | 2/2017 | Hennig et al. | |
| 2017/0191937 A1* | 7/2017 | Levenson | G01N 21/6445 |
| 2017/0249548 A1 | 8/2017 | Nelson et al. | |
| 2017/0343477 A1* | 11/2017 | Santori | G01J 3/18 |
| 2017/0343784 A1* | 11/2017 | Wu | G02B 21/004 |
| 2018/0012356 A1* | 1/2018 | Madabhushi | G06T 7/0012 |
| 2018/0028079 A1 | 2/2018 | Gurevich et al. | |
| 2018/0064409 A1 | 3/2018 | Schmidt-Richberg et al. | |
| 2018/0286038 A1* | 10/2018 | Jalali | G01N 15/147 |
| 2019/0188446 A1* | 6/2019 | Wu | G06V 20/695 |
| 2019/0251330 A1 | 8/2019 | Cotte et al. | |
| 2019/0333199 A1* | 10/2019 | Ozcan | G06T 3/4046 |
| 2019/0384047 A1 | 12/2019 | Johnson et al. | |
| 2019/0392580 A1 | 12/2019 | Kapil et al. | |
| 2020/0066407 A1 | 2/2020 | Stumpe et al. | |
| 2020/0372635 A1 | 11/2020 | Veidman et al. | |
| 2021/0264214 A1 | 8/2021 | Ozcan et al. | |
| 2023/0030424 A1* | 2/2023 | Ozcan | G06F 18/24137 |

FOREIGN PATENT DOCUMENTS

| | | |
|---|---|---|
| EP | 2921990 A2 | 9/2015 |
| WO | WO 2013/187148 | 12/2013 |
| WO | WO 2017/053592 | 3/2017 |
| WO | WO 2017/196885 | 11/2017 |
| WO | WO 2018/165590 | 9/2018 |
| WO | WO 2020/018154 | 1/2020 |

OTHER PUBLICATIONS

Response to the First Examination Report dated Oct. 13, 2022 for Indian Patent Application No. 202037045753, (25 pages).
The extended European search report dated May 7, 2021 for European Patent Application No. European patent application 19776693.4 (8 pages).
Communication pursuant to Rules 70(2) and 70a(2) EPC dated May 26, 2021 for European Patent Application No. European patent application 19776693.4 (1 page).
Response to the extended European search report dated Dec. 2, 2021 for European Patent Application No. European patent application 19776693.4 (16 pages).
Neslihan Bayramoglu et al., Towards Virtual H&E Staining of Hyperspectral Lung Histology Images Using Conditional Generative Adversarial Networks, 2017 IEEE International Conference on Computer Vision Workshops (ICCVW), Oct. 22, 2017, pp. 64-71, XP055497287.
Erik A. Burlingame et al., Shift: speedy histopathological-to-immunofluorescent translation of whole slide images using conditional generative adversarial networks, Progress in Biomedical Optics and Imaging, SPIE—International Society for Optical Engineering, Bellingham, WA, US, vol. 10581, Mar. 6, 2018 (Mar. 6, 2018), pp. 1058105-1058105.
Liang Han et al., Transferring Microscopy Image Modalities with Conditional Generative Adversarial Networks, 2017 IEEE Conference on Computer Vision and Pattern Recognition Workshops (CVPRW), Jul. 21, 2017 (Jul. 21, 2017), pp. 851-859, XP033145860.
Notice of Reasons for Refusal dated Jan. 18, 2023 for Japanese Patent Application No. 2020-552396, (8 pages).
Neslihan Bayramoglu et al., Towards Virtual H&E Staining of Hyperspectral Lung Histology Images Using Conditional Generative Adversarial Networks, 2017, IEEE International Conference on Computer Vision Workshops (ICCVW), IEEE, 2017, 71, ISR D3/ESRD (8 pages).
PCT International Preliminary Report on Patentability (Chapter I of the Patent Cooperation Treaty) for PCT/US2019/025020, Applicant: The Regents of the University of California, Form PCT/IB/326 and 373, dated Oct. 15, 2020 (6 pages).
First Examination Report dated Feb. 27, 2023 for European Patent Application No. 19776693.4, (7 pages).
Sinno Jialin Pan et al., A Survey on Transfer Learning, IEEE Transactions on Knowledge and Data Engineering, vol. 22, No. 10, 1345-1359 (Oct. 2010).
Response to First Examination Report dated Jul. 10, 2023 for European Patent Application No. 19776693.4, (16 pages).
Response to office action dated Apr. 21, 2023 in Japanese Patent Application No. 2020-552396, (13 pages).
Yan Zhang et al., High-Throughput, Label-Free and Slide-Free Histological Imaging by Computational Microscopy and Unsupervised Learning, Adv. Sci. 2022, 9, 2102358 (14 pages).

(56) References Cited

OTHER PUBLICATIONS

PCT Notification of Transmittal of the International Search Report and Written Opinion for PCT/US2019/021471, dated Jun. 19, 2019, 7 pages.

Bayramoglu et al., Towards Virtual H&E Staining of Hyperspectral Lung Histology Images Using Conditional Generative Adversarial Networks, 2017 IEEE International Conference on Computer Vision Workshops (ICCVW). Retrieved on May 30, 2019. Retrieved from the internet <URL:https://ieeexplore.ieee.org/document/8265226>.

Rivenson et al., Deep Learning-based virtual histology staining using auto-fluorescence of label-free tissue, Nature Biomedical Engineering (2019). Retrieved on May 24, 2019. Retrieved from: <URL:https://arxiv.org/abs/1803.11293>.

Croce et al., Autofluorescence spectroscopy and imaging: a tool for biomedical research and diagnosis, European Journal of Histochemistry 2014; vol. 58:2461.

Fereidouni et al., Microscopy with ultraviolet surface excitation for rapid slide-free histology, Nat Biomed Eng. 2017; 1:957-966.

Giacomelli et al., (2016) Virtual Hematoxylin and Eosin Transillumination Microscopy Using Epi-Fluorescence Imaging. PLoS One 11(8):e0159337. Doi:10.1371/journal.pone.0159337.

Glaser et al., Light-sheet microscopy for slide-free non-destructive pathology of large clinical specimens, Nat Biomed Eng. Jul. 2017; 1(7): doi:10.1038/s41551-017-0084.

Goodfellow et al., Generative Adversarial Nets, http://www.github.com/goodfeli/adversarial, Jun. 10, 2014.

Hamel et al., Transfer Learning in MIR: Sharing Learned Latent Representations for Music Audio Classification and Similarity, 2013 International Society for Music Information Retrieval.

He et al., Deep Residual Learning for Image Recognition, arXiv:1512.03385v1 [cs.CV] Dec. 10, 2015.

He et al., Identity Mappings in Deep Residual Networks, arXiv:1603.05027v3 [cs.CV] Jul. 25, 2016.

Jamme et al., DUV Autofluorescence Microscopy for Cell Biology and Tissue Histology Biology of the Cell Biology of the Cell, Biology of the Cell, Wiley, 2013, 105 (7), pp. 277-288. 10.1111/boc.201200075. hal-01485578.

Ji et al., Rapid, label-free detection of brain tumors with stimulated Raman scattering microscopy, Sci Transl Med. Sep. 4, 2013; 5(201): 201ra119. doi:10.1126/scitranslmed.3005954.

Kingma et al., ADAM: A Method for Stochastic Optimization, arXiv:1412.6980v9 [cs.LG] Jan. 30, 2017.

Liu et al., Detecting Cancer Metastases on Gigapixel Pathology Images, arXiv:1703.02442v2 [cs.CV] Mar. 8, 2017.

Lowe, Distinctive Image Features from Scale-Invariant Keypoints, Accepted for publication in the International Journal of Computer Vision, 2004.

Lu et al., Label-free DNA imaging in vivo with stimulated Raman scattering microscopy, 11624-11629, PNAS, Sep. 15, 2015, vol. 112, No. 37, www.pnas.org/cgi/doi/10.1073/pnas.1515121112.

Monici, Cell and tissue autofluorescence research and diagnostic application, Biotechnology Annual Review, vol. 11, ISSN: 1387-2656, DOI: 10.1016/S1387-2656(05)11007-2.

Rivenson et al., Phase recovery and holographic image reconstruction using deep learning in neural networks, Light: Science & Applications (2018) 7, 17141; doi:10.1038/lsa.2017.141.

Rivenson et al., Deep learning enhanced mobile-phone microscopy, (2017).

Rivenson et al., Deep Learning Microscopy, (2017).

Ronneberger et al., U-Net: Convolutional Networks for Biomedical Image Segmentation, arXiv:1505.04597v1 [cs.CV] May 18, 2015; http://lmb.informatik.uni-freiburg.de/.

Tao et al., Assessment of breast pathologies using nonlinear microscopy, 15304-15309, PNAS, Oct. 28, 2014, vol. 111, No. 43, www.pnas.org/cgi/doi/10.1073/pnas.1416955111.

Torr et al., MLESAC: A New Robust Estimator with Application to Estimating Image Geometry, Computer Vision and Image Understanding 78, 138-156 (2000), doi:10.1006/cviu.1999.0832, available online at http://www.idealibrary.com.

Tu et al., Stain-free histopathology by programmable supercontinuum pulses, Nat Photonics. Aug. 2016 ; 10(8):534-540. doi:10.1038/nphoton.2016.94.

Vacoc et al., Three-dimensional microscopy of the tumor microenvironment in vivo using optical frequency domain imaging, Nat Med. Oct. 2009 ; 15(10): 1219-1223. doi:10.1038/nm.1971.

Witte et al., Label-free live brain imaging and targeted patching with third-harmonic generation microscopy, 5970-5975, PNAS, Apr. 12, 2011, vol. 108, No. 15, www.pnas.org/cgi/doi/10.1073/pnas.1018743108.

Wu et al., Extended depth of field in holographic image reconstruction using deep learning based auto-focusing and phase recovery, arXiv1803.08138 Mar. 2018.

PCT Notification of Transmittal of the International Search Report and Written Opinion for PCT/US2019/025014, dated Jun. 11, 2019, 9 pages.

Office Action dated Nov. 9, 2023 for U.S. Appl. No. 17/261,542, (12 pages).

Office Action dated May 9, 2023 for U.S. Appl. No. 17/261,542, (21 pages).

George Barbastathis et al., On the use of deep learning for computation imaging, Optica, Jul. 25, 2019, pp. 921-943.

George Barbastathis et al., On the use of deep learning for computation imaging, Optica, Aug. 2019.

Response to Office Action dated Aug. 9, 2023 for U.S. Appl. No. 17/261,542, (9 pages).

Notification of the First Office Action dated Nov. 4, 2023, for Chinese Patent Application No. 2019800291722.

* cited by examiner

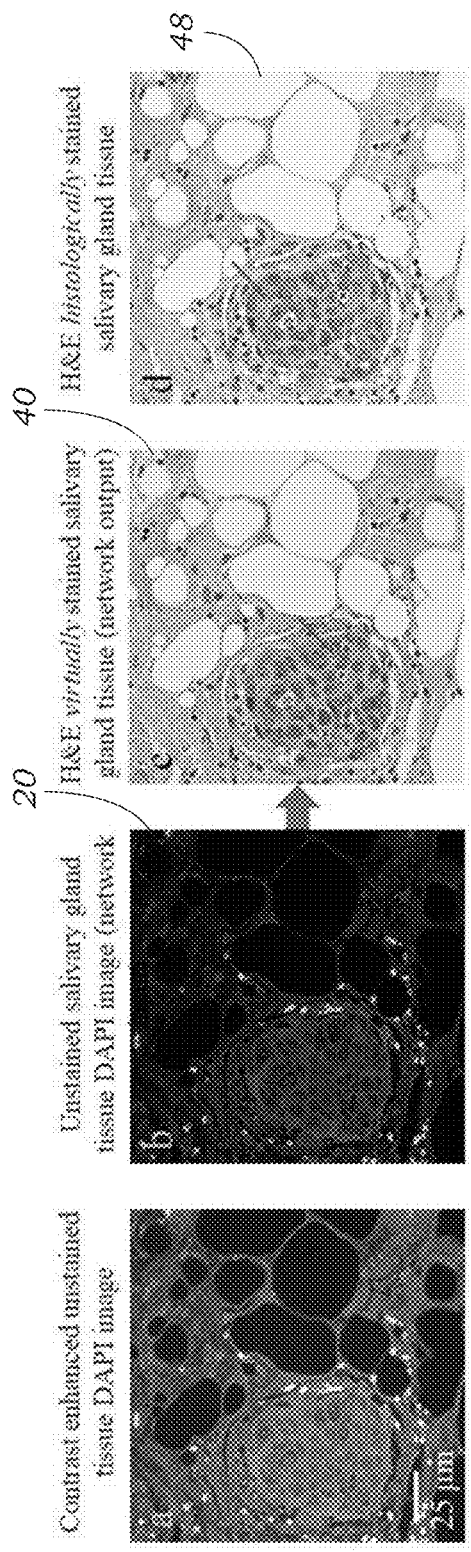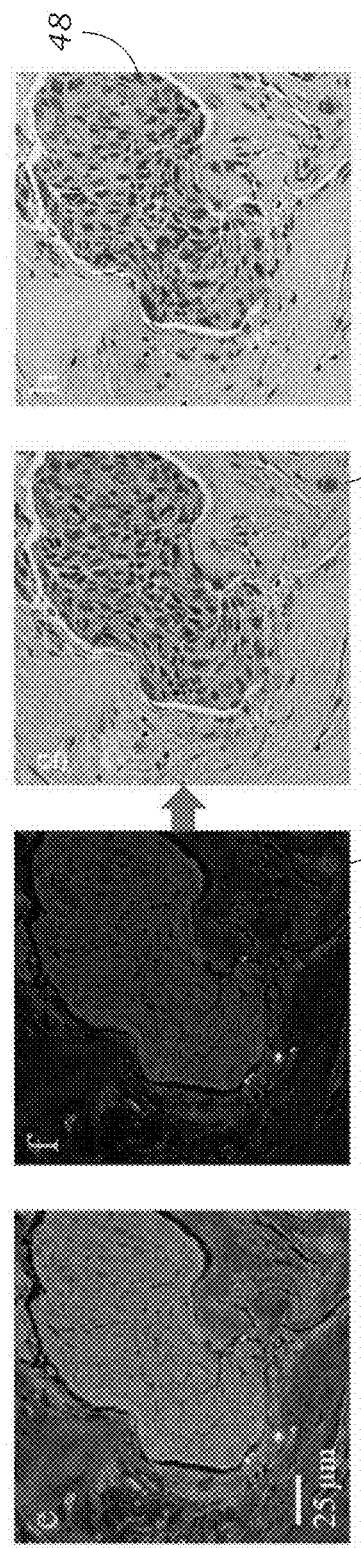

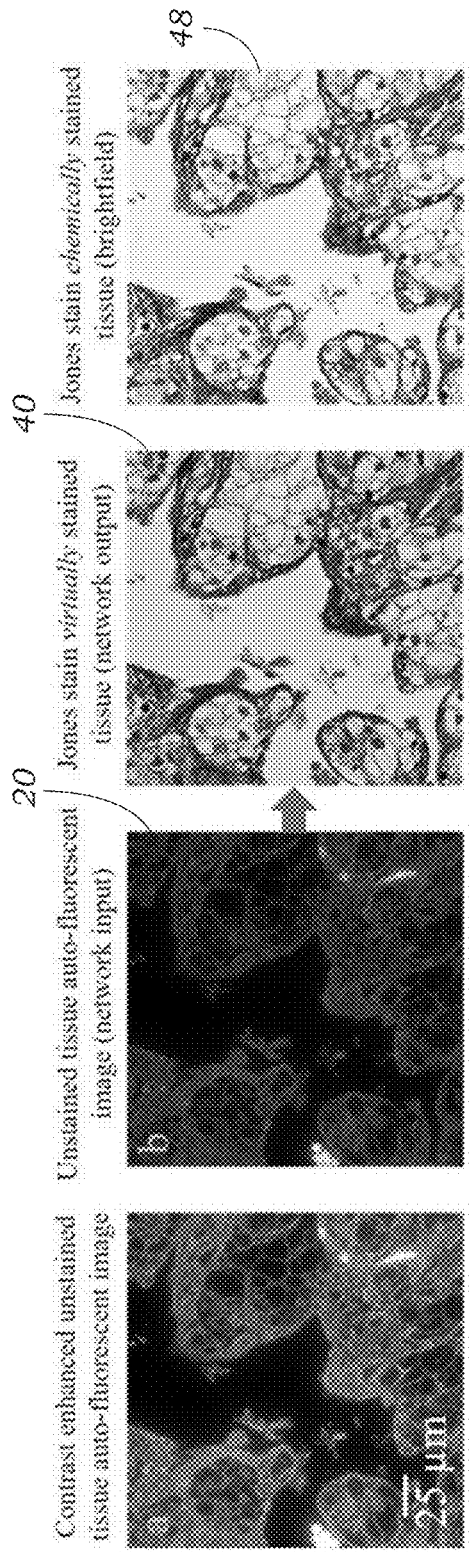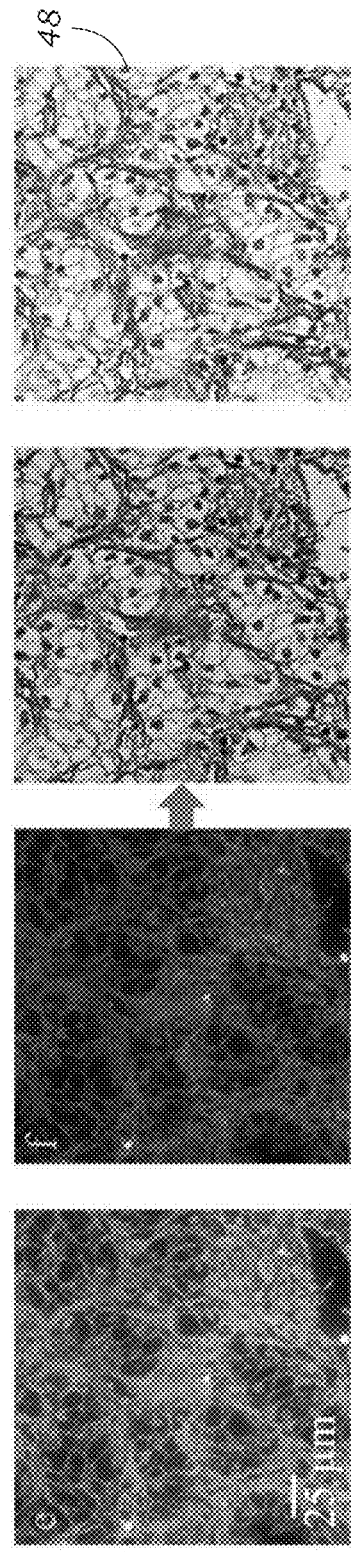

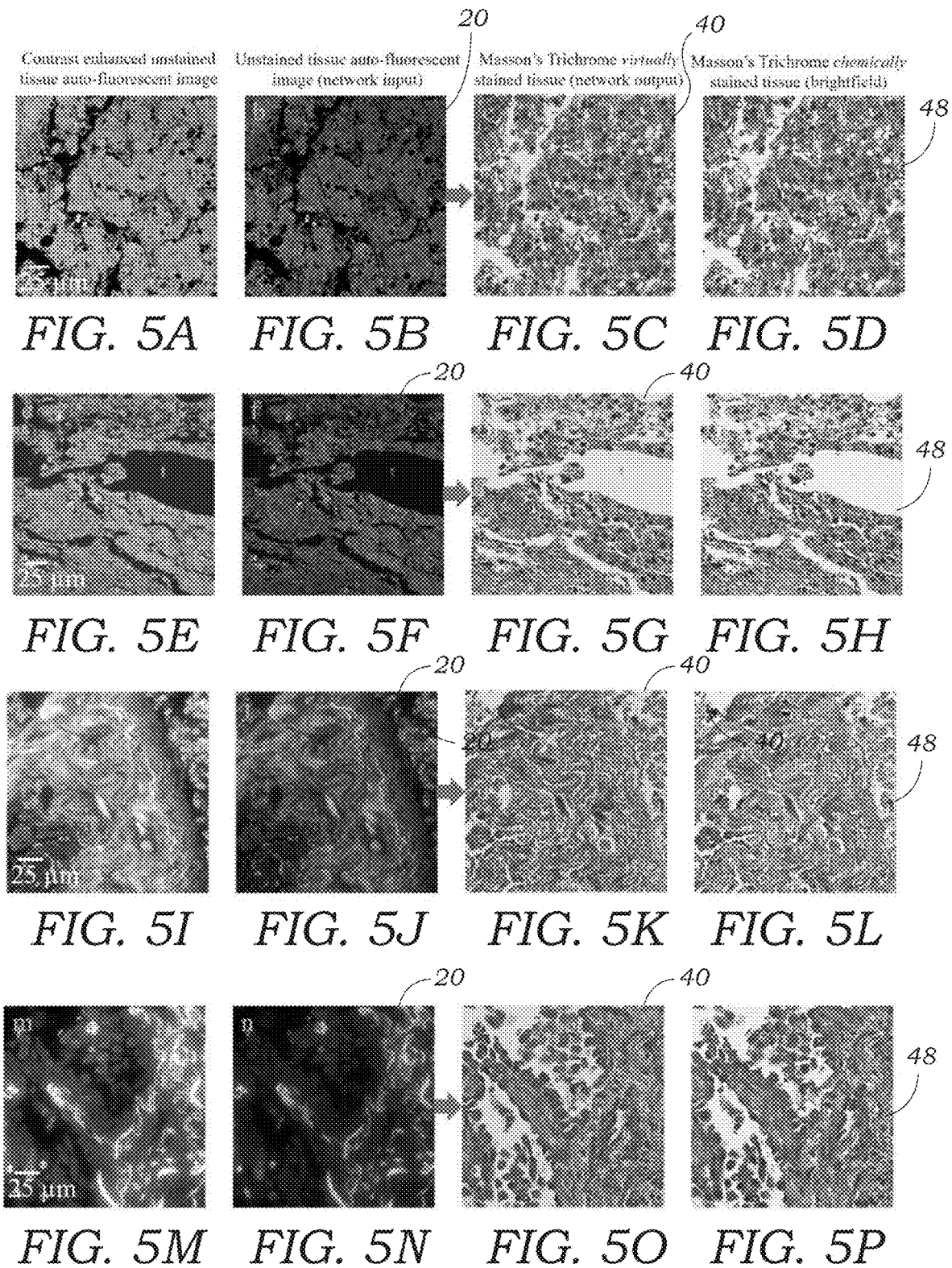

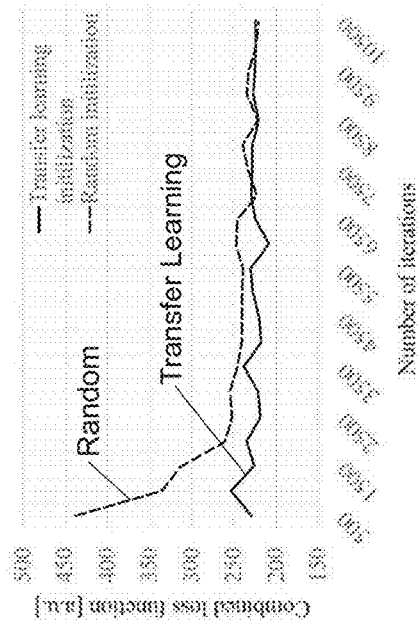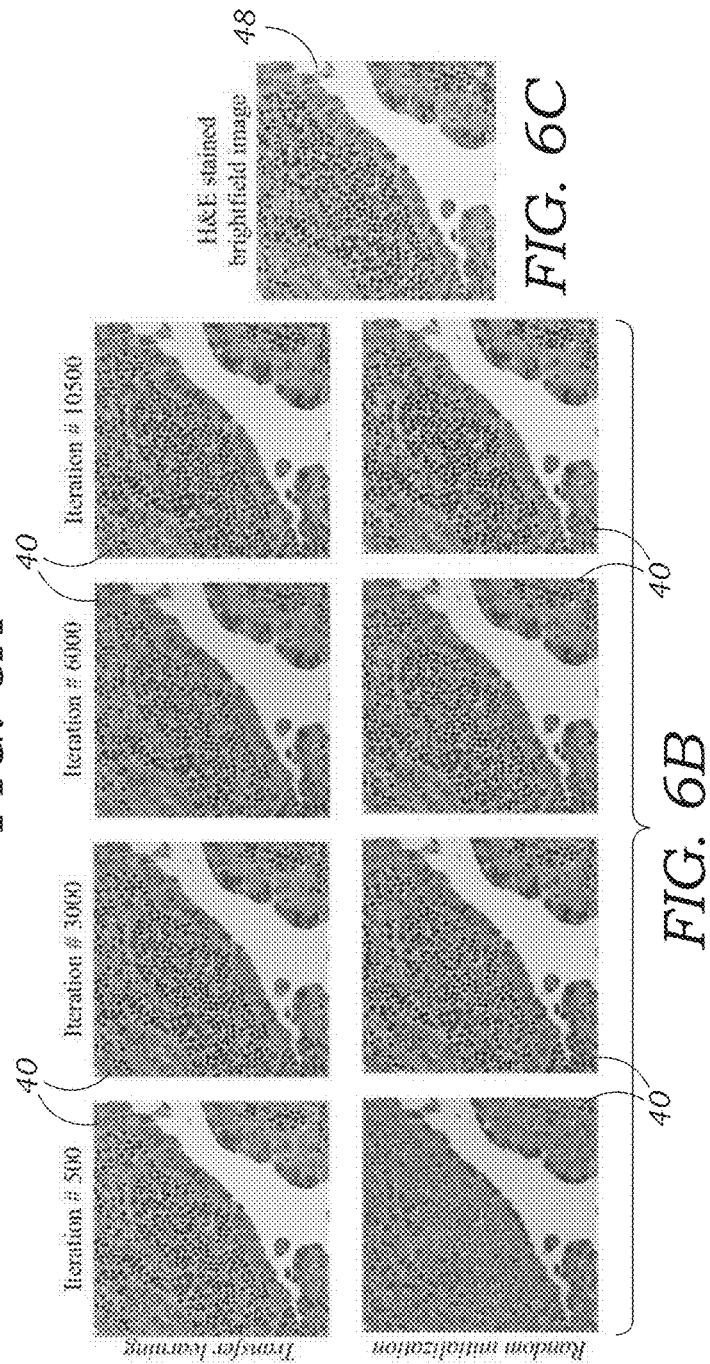
FIG. 6A
FIG. 6B
FIG. 6C

METHOD AND SYSTEM FOR DIGITAL STAINING OF LABEL-FREE FLUORESCENCE IMAGES USING DEEP LEARNING

RELATED APPLICATION

This Application is a U.S. National Stage filing under 35 U.S.C. § 371 of International Application No. PCT/US2019/025020, filed Mar. 29, 2019, which claims priority to U.S. Provisional Patent Application No. 62/651,005 filed on Mar. 30, 2018, which are hereby incorporated by reference. Priority is claimed pursuant to 35 U.S.C. §§ 119, 371 and any other applicable statute.

TECHNICAL FIELD

The technical field generally relates to methods and systems used to image unstained (i.e., label-free) tissue. In particular, the technical field relates to microscopy methods and systems that utilize deep neural network learning for digitally or virtually staining of images of unstained or unlabeled tissue. Deep learning in neural networks, a class of machine learning algorithms, are used to digitally stain images of label-free tissue sections into images that are equivalent to microscopy images of the same samples that are stained or labelled.

BACKGROUND

Microscopic imaging of tissue samples is a fundamental tool used for the diagnosis of various diseases and forms the workhorse of pathology and biological sciences. The clinically-established gold standard image of a tissue section is the result of a laborious process, which includes the tissue specimen being formalin-fixed paraffin-embedded (FFPE), sectioned to thin slices (typically ~2-10 µm), labeled/stained and mounted on a glass slide, which is then followed by its microscopic imaging using e.g., a brightfield microscope. All these steps use multiple reagents and introduce irreversible effects on the tissue. There have been recent efforts to change this workflow using different imaging modalities. Attempts have been made to imaged fresh, non-paraffin-embedded tissue samples using non-linear microscopy methods based on e.g., two-photon fluorescence, second harmonic generation, third-harmonic generation as well as Raman scattering. Other attempts have used a controllable super-continuum source to acquire multi-modal images for chemical analysis of fresh tissue samples. These methods require using ultra-fast lasers or super-continuum sources, which might not be readily available in most settings and require relatively long scanning times due to weaker optical signals. In addition to these, other microscopy methods for imaging non-sectioned tissue samples have also emerged by using UV-excitation on stained samples, or by taking advantage of the fluorescence emission of biological tissue at short wavelengths.

In fact, fluorescence signal creates some unique opportunities for imaging tissue samples by making use of the fluorescent light emitted from endogenous fluorophores. It has been demonstrated that such endogenous fluorescence signatures carry useful information that can be mapped to functional and structural properties of biological specimen and therefore have been used extensively for diagnostics and research purposes. One of the main focus areas of these efforts has been the spectroscopic investigation of the relationship between different biological molecules and their structural properties under different conditions. Some of these well-characterized biological constituents include vitamins (e.g., vitamin A, riboflavin, thiamin), collagen, coenzymes, fatty acids, among others.

While some of the above discussed techniques have unique capabilities to discriminate e.g., cell types and subcellular components in tissue samples using various contrast mechanisms, pathologists as well as tumor classification software are in general trained for examining "gold standard" stained tissue samples to make diagnostic decisions. Partially motivated by this, some of the above-mentioned techniques have been augmented to create pseudo-Hematoxylin and Eosin (H&E) images, which are based on a linear approximation that relates the fluorescence intensity of an image to the dye concentration per tissue volume, using empirically determined constants that represent the mean spectral response of various dyes embedded in the tissue. These methods also used exogenous staining to enhance the fluorescence signal contrast in order to create virtual H&E images of tissue samples.

SUMMARY

In one embodiment, a system and method are provided that utilizes a trained deep neural network that is used for the digital or virtual staining of label-free thin tissue sections or other samples using their fluorescence images obtained from chemically unstained tissue (or other samples). Chemically unstained tissue refers to the lack of standard stains or labels used in histochemical staining of tissue. The fluorescence of chemically unstained tissue may include auto-fluorescence of tissue from naturally occurring or endogenous fluorophores or other endogenous emitters of light at frequencies different from the illumination frequency (i.e., frequency-shifted light). Fluorescence of chemically unstained tissue may further include fluorescence of tissue from exogenously added fluorescent labels or other exogenous emitters of light. Samples are imaged with a fluorescence microscope such as a wide-field fluorescence microscope (or a standard fluorescence microscope). The microscope may utilize a standard near-UV excitation/emission filter set or other excitation/emission light source/filter sets that are known to those skilled in the art. The digital or virtual staining is performed, in some embodiments, on a single fluorescence image obtained of the sample by using, in on preferred embodiment, a trained deep neural network.

In one embodiment, the trained deep neural network is a Convolutional Neural Network (CNN) which is trained using a Generative Adversarial Networks (GAN) model to match the corresponding brightfield microscopic images of tissue samples after they are labeled with a certain histology stain. In this embodiment, a fluorescence image of the unstained sample (e.g., tissue) is input to the trained deep neural network to generate the digitally stained image. Therefore, in this embodiment, the histochemical staining and brightfield imaging steps are completely replaced by the use of the trained deep neural network which generates the digitally stained image. As explained herein, the network inference performed by the trained neural network is fast, taking in some embodiments, less than a second using a standard desktop computer for an imaging field-of-view of ~0.33 mm×0.33 mm using e.g., a 40× objective lens. Using a 20× objective for scanning tissue, a network inference time of 1.9 seconds/mm$^2$ was achieved.

The deep learning-based digital/virtual histology staining method using auto-fluorescence has been demonstrated by imaging label-free human tissue samples including salivary gland, thyroid, kidney, liver, lung and skin, where the trained deep neural network output created equivalent images, substantially matching with the images of the same samples that were labeled with three different stains, i.e., H&E (salivary gland and thyroid), Jones stain (kidney) and Masson's Trichrome (liver and lung). Because the trained deep neural network's input image is captured by a conventional fluorescence microscope with a standard filter set, this approach has transformative potential to use unstained tissue samples for pathology and histology applications, entirely bypassing the histochemical staining process, saving time and the attendant costs. This includes the cost of labor, reagents, the additional time involved in staining processes, and the like. For example, for the histology stains that were approximated using the digital or virtual staining process described herein, each staining procedure of a tissue section on average takes ~45 min (H&E) and 2-3 hours (Masson's Trichrome and Jones stain), with an estimated cost, including labor, of $2-5 for H&E and >$16-35 for Masson's Trichrome and Jones stain. Furthermore, some of these histochemical staining processes require time-sensitive steps, demanding the expert to monitor the process under a microscope, which makes the entire process not only lengthy and relatively costly, but also laborious. The system and method disclosed herein bypasses all these staining steps, and also allows the preservation of unlabeled tissue sections for later analysis, such as micromarking of sub-regions of interest on the unstained tissue specimen that can be used for more advanced immunochemical and molecular analysis to facilitate e.g., customized therapies. Furthermore, the staining efficacy of this approach for whole slide images (WSIs) corresponding to some of these samples was blindly evaluated by a group of pathologists, who were able to recognize histopathological features with the digital/virtual staining technique, achieving a high degree of agreement with the histologically stained images of the same samples.

Further, this deep learning-based digital/virtual histology staining framework can be broadly applied to other excitation wavelengths or fluorescence filter sets, as well as to other microscopy modalities (such as non-linear microscopy) that utilize additional endogenous contrast mechanisms. In the experiments, sectioned and fixed tissue samples were used to be able to provide meaningful comparisons to the results of the standard histochemical staining process. However, the presented approach would also work with non-fixed, non-sectioned tissue samples, potentially making it applicable to use in surgery rooms or at the site of a biopsy for rapid diagnosis or telepathology applications. Beyond its clinical applications, this method could broadly benefit histology field and its applications in life science research and education.

In one embodiment, a method of generating a digitally stained microscopic image of a label-free sample includes providing a trained, deep neural network that is run using image processing software executed using one or more processors of a computing device, wherein the trained, deep neural network is trained with a plurality of matched chemically stained images or image patches and their corresponding fluorescence images or image patches of the same sample. The label-free sample may include tissues, cells, pathogens, biological fluid smears, or other micro-objects of interest. In some embodiments, the deep neural network may be trained using one or more tissue type/chemical stain type combinations. For example, this may include tissue type A with stain #1, stain #2, stain #3, etc. In some embodiments, the deep neural network may be trained using tissue that has been stained with multiple stains.

A fluorescence image of the sample is input to the trained, deep neural network. The trained, deep neural network then outputs a digitally stained microscopic image of the sample based on the input fluorescence image of the sample. In one embodiment, the trained, deep neural network is a convolutional neural network (CNN). This may include a CNN that uses a Generative Adversarial Network (GAN) model. The fluorescence input image of the sample is obtained using a fluorescence microscope and an excitation light source (e.g., UV or near UV emitting light source). In some alternative embodiments, multiple fluorescence images are input into the trained, deep neural network. For example, one fluorescence image may be obtained at a first filtered wavelength or wavelength range while another fluorescence image may be obtained at a second filtered wavelength or wavelength range. These two fluorescence images are then input into the trained, deep neural network to output a single digitally/virtually stained image. In another embodiment, the obtained fluorescence image may be subject to one or more linear or non-linear pre-processing operations selected from contrast enhancement, contrast reversal, image filtering which may be input alone or in combination with the obtained fluorescence image into the trained, deep neural network.

For example, in another embodiment, a method of generating a digitally stained microscopic image of a label-free sample includes providing a trained, deep neural network that is executed by image processing software using one or more processors of a computing device, wherein the trained, deep neural network is trained with a plurality of matched chemically stained images or image patches and their corresponding fluorescence images or image patches of the same sample. A first fluorescence image of the sample is obtained using a fluorescence microscope and wherein fluorescent light at a first emission wavelength or wavelength range is emitted from endogenous fluorophores or other endogenous emitters of frequency-shifted light within the sample. A second fluorescence image of the sample is obtained using a fluorescence microscope and wherein fluorescent light at a second emission wavelength or wavelength range is emitted from endogenous fluorophores or other endogenous emitters of frequency-shifted light within the sample. The first and second fluorescence images may be obtained by using different excitation/emission wavelength combinations. The first and second fluorescence images of the sample are then input to the trained, deep neural network, the trained, deep neural network outputting the digitally stained microscopic image of the sample that is substantially equivalent to a corresponding brightfield image of the same sample that has been chemically stained.

In another embodiment, a system for generating digitally stained microscopic images of a chemically unstained sample includes a computing device having image processing software executed thereon or thereby, the image processing software comprising a trained, deep neural network that is executed using one or more processors of the computing device. The trained, deep neural network is trained with a plurality of matched chemically stained images or image patches and their corresponding fluorescence images or image patches of the same sample. The image processing software is configured to receive one or more fluorescence image(s) of the sample and output the digitally stained microscopic image of the sample that is substantially equivalent to a corresponding brightfield image of the same sample that has been chemically stained.

BRIEF DESCRIPTION OF THE DRAWINGS

FIGS. 3A-3H illustrate digital/virtual staining results that match the chemically stained H&E samples. The first two (2) columns (FIGS. 3A and 3E) show the auto-fluorescence images of unstained salivary gland tissue sections (used as input to the deep neural network), and the third column (FIGS. 3C and 3G) shows the digital/virtual staining results. The last column (FIGS. 3D and 3H) shows the brightfield images of the same tissue sections, after the histochemical staining process. Evaluation of both FIG. 3C and FIG. 3D demonstrates a small island of infiltrating tumor cells within subcutaneous fibro-adipose tissue. Note that the nuclear detail, including distinction of nucleoli (arrows in 3C and 3D) and chromatin texture, is clearly appreciated in both panels. Similarly, in FIGS. 3G and 3H the H&E stains demonstrate infiltrating squamous cell carcinoma. The desmoplastic reaction with edematous myxoid change (asterisk in FIGS. 3G and 3H) in the adjacent stroma is clearly identifiable in both stains/panels.

FIGS. 4A-4H illustrate digital/virtual staining results to match the chemically stained Jones samples. The first two (2) columns (FIGS. 4A, 4E) show the auto-fluorescence images of unstained kidney tissue sections (used as input to the deep neural network), and the third column (FIGS. 4C and 4G), shows the digital/virtual staining results. The last column (FIGS. 4D, 4H) shows the brightfield images of the same tissue sections, after the histochemical staining process.

FIGS. 5A-5P illustrate digital/virtual staining results to match the Masson's Trichrome stain for liver and lung tissue sections. The first two (2) columns show the auto-fluorescence images of an unstained liver tissue section (rows 1 and 2—FIGS. 5A, 5B, 5E, 5F) and an unstained lung tissue section (rows 3 and 4—FIGS. 5I, 5J, 5M, 5N), used as input to the deep neural network. The third column (FIGS. 5C, 5G, 5K, 5O) shows the digital/virtual staining results for these tissue samples. The last column (FIGS. 5D, 5H, 5L, 5P) shows the brightfield images of the same tissue sections, after the histochemical staining process.

FIG. 6A illustrates a graph of combined loss function vs. number of iterations for random initialization and transfer learning initialization. FIG. 6A illustrates how superior convergence is achieved using transfer learning. A new deep neural network is initialized using the weights and biases learned from the salivary gland tissue sections to achieve virtual staining of thyroid tissue with H&E. Compared to random initialization, transfer learning enables much faster convergence, also achieving a lower local minimum.

FIG. 6B illustrates network output images at different stages of the learning process for both random initialization and transfer learning to better illustrate the impact of the transfer learning to translate the presented approach to new tissue/stain combinations.

FIG. 6C illustrates the corresponding H&E chemically stained brightfield image.

DETAILED DESCRIPTION OF THE ILLUSTRATED EMBODIMENTS

Figure 1:
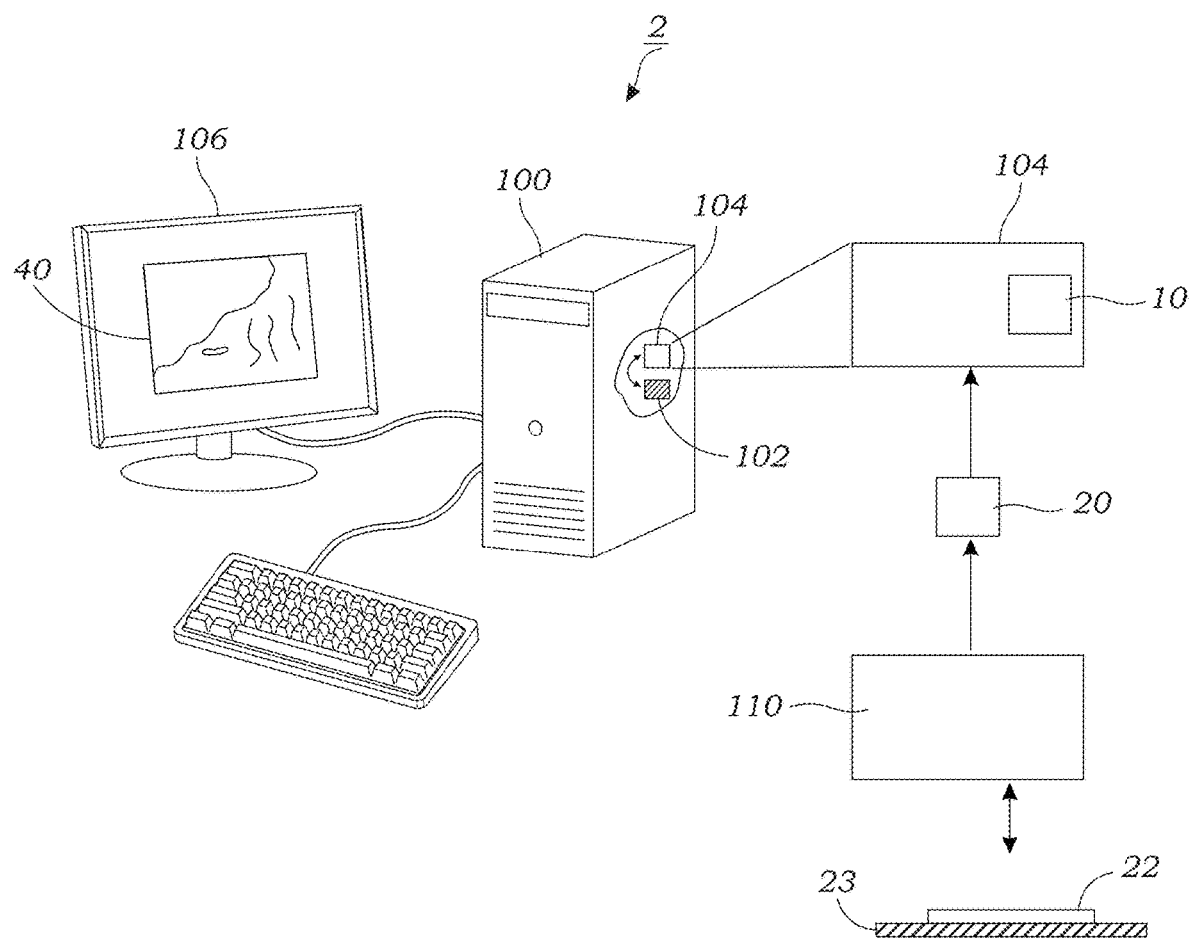
FIG. 1 schematically illustrates a system that is used to generate a digitally/virtually stained output image of a sample from an unstained microscope image of the sample according to one embodiment.

FIG. 1 schematically illustrates one embodiment of a system 2 for outputting digitally stained images 40 from an input microscope image 20 of a sample 22. As explained herein, the input image 20 is a fluorescence image 20 of a sample 22 (such as tissue in one embodiment) that is not stained or labeled with a fluorescent stain or label. Namely, the input image 20 is an autofluorescence image 20 of the sample 22 in which the fluorescent light that is emitted by the sample 22 is the result of one or more endogenous fluorophores or other endogenous emitters of frequency-shifted light contained therein. Frequency-shifted light is light that is emitted at a different frequency (or wavelength) that differs from the incident frequency (or wavelength). Endogenous fluorophores or endogenous emitters of frequency-shifted light may include molecules, compounds, complexes, molecular species, biomolecules, pigments, tissues, and the like. In some embodiments, the input image 20 (e.g., the raw fluorescent image) is subject to one or more linear or non-linear pre-processing operations selected from contrast enhancement, contrast reversal, image filtering. The system includes a computing device 100 that contains one or more processors 102 therein and image processing software 104 that incorporates the trained, deep neural network 10 (e.g., a convolutional neural network as explained herein in one or more embodiments). The computing device 100 may include, as explained herein, a personal computer, laptop, mobile computing device, remote server, or the like, although other computing devices may be used (e.g., devices that incorporate one or more graphic processing units (GPUs)) or other application specific integrated circuits (ASICs). GPUs or ASICs can be used to accelerate training as well as final image output. The computing device 100 may be associated with or connected to a monitor or display 106 that is used to display the digitally stained images 40. The display 106 may be used to display a Graphical User Interface (GUI) that is used by the user to display and view the digitally stained images 40. In one embodiment, the user may be able to trigger or toggle manually between multiple different digital/virtual stains for a particular sample 22 using, for example, the GUI. Alternatively, the triggering or toggling between different stains may be done automatically by the computing device 100. In one preferred embodiment, the trained, deep neural network 10 is a Convolution Neural Network (CNN).

For example, in one preferred embodiment as is described herein, the trained, deep neural network 10 is trained using a GAN model. In a GAN-trained deep neural network 10, two models are used for training. A generative model is used that captures data distribution while a second model estimates the probability that a sample came from the training data rather than from the generative model. Details regarding GAN may be found in Goodfellow et al., Generative Adversarial Nets., Advances in Neural Information Processing Systems, 27, pp. 2672-2680 (2014), which is incorporated by reference herein. Network training of the deep neural network 10 (e.g., GAN) may be performed the same or different computing device 100. For example, in one embodiment a personal computer may be used to train the GAN although such training may take a considerable amount of time. To accelerate this training process, one or more dedicated GPUs may be used for training. As explained herein, such training and testing was performed on GPUs obtained from a commercially available graphics card. Once the deep neural network 10 has been trained, the deep neural network 10 may be used or executed on a different computing device 110 which may include one with less computational resources used for the training process (although GPUs may also be integrated into execution of the trained deep neural network 10).

The image processing software 104 can be implemented using Python and TensorFlow although other software packages and platforms may be used. The trained deep neural network 10 is not limited to a particular software platform or programming language and the trained deep neural network 10 may be executed using any number of commercially available software languages or platforms. The image processing software 104 that incorporates or runs in coordination with the trained, deep neural network 10 may be run in a local environment or a remove cloud-type environment. In some embodiments, some functionality of the image processing software 104 may run in one particular language or platform (e.g., image normalization) while the trained deep neural network 10 may run in another particular language or platform. Nonetheless, both operations are carried out by image processing software 104.

As seen in FIG. 1, in one embodiment, the trained, deep neural network 10 receives a single fluorescence image 20 of an unlabeled sample 22. In other embodiments, for example, where multiple excitation channels are used (see melanin discussion herein), there may be multiple fluorescence images 20 of the unlabeled sample 22 that are input to the trained, deep neural network 10 (e.g., one image per channel). The fluorescence images 20 may include a wide-field fluorescence image 20 of an unlabeled tissue sample 22. Wide-field is meant to indicate that a wide field-of-view (FOV) is obtained by scanning of a smaller FOV, with the wide FOV being in the size range of 10-2,000 mm$^2$. For example, smaller FOVs may be obtained by a scanning fluorescent microscope 110 that uses image processing software 104 to digitally stitch the smaller FOVs together to create a wider FOV. Wide FOVs, for example, can be used to obtain whole slide images (WSI) of the sample 22. The fluorescence image is obtained using an imaging device 110. For the fluorescent embodiments described herein, this may include a fluorescence microscope 110. The fluorescent microscope 110 includes an excitation light source that illuminates the sample 22 as well as one or more image sensor(s) (e.g., CMOS image sensors) for capturing fluorescent light that is emitted by fluorophores or other endogenous emitters of frequency-shifted light contained in the sample 22. The fluorescence microscope 110 may, in some embodiments, include the ability to illuminate the sample 22 with excitation light at multiple different wavelengths or wavelength ranges/bands. This may be accomplished using multiple different light sources and/or different filter sets (e.g., standard UV or near-UV excitation/emission filter sets). In addition, the fluorescence microscope 110 may include, in some embodiments, multiple filter sets that can filter different emission bands. For example, in some embodiments, multiple fluorescence images 20 may be captured, each captured at a different emission band using a different filter set.

The sample 22 may include, in some embodiments, a portion of tissue that is disposed on or in a substrate 23. The substrate 23 may include an optically transparent substrate in some embodiments (e.g., a glass or plastic slide or the like). The sample 22 may include a tissue sections that are cut into thin sections using a microtome device or the like. Thin sections of tissue 22 can be considered a weakly scattering phase object, having limited amplitude contrast modulation under brightfield illumination. The sample 22 may be imaged with or without a cover glass/cover slip. The sample may involve frozen sections or paraffin (wax) sections. The tissue sample 22 may be fixed (e.g., using formalin) or unfixed. The tissue sample 22 may include mammalian (e.g., human or animal) tissue or plant tissue. The sample 22 may also include other biological samples, environmental samples, and the like. Examples include particles, cells, cell organelles, pathogens, or other microscale objects of interest (those with micrometer-sized dimensions or smaller). The sample 22 may include smears of biological fluids or tissue. These include, for instance, blood smears, Papanicolaou or Pap smears. As explained herein, for the fluorescent-based embodiments, the sample 22 includes one or more naturally occurring or endogenous fluorophores that fluoresce and are captured by the fluorescent microscope device 110. Most plant and animal tissues show some autofluorescence when excited with ultraviolet or near ultra-violet light. Endogenous fluorophores may include by way of illustration proteins such as collagen, elastin, fatty acids, vitamins, flavins, porphyrins, lipofuscins, co-enzymes (e.g., NAD(P)H). In some optional embodiments, exogenously added fluorescent labels or other exogenous emitters of light may also be added. As explained herein, the sample 22 may also contain other endogenous emitters of frequency-shifted light.

The trained, deep neural network 10 in response to the input image 20 outputs or generates a digitally stained or labelled output image 40. The digitally stained output image 40 has "staining" that has been digitally integrated into the stained output image 40 using the trained, deep neural network 10. In some embodiments, such as those involved tissue sections, the trained, deep neural network 10 appears to a skilled observer (e.g., a trained histopathologist) to be substantially equivalent to a corresponding brightfield image of the same tissue section sample 22 that has been chemically stained. Indeed, as explained herein, the experimental results obtained using the trained, deep neural network 10 show that trained pathologists were able to recognize histopathologic features with both staining techniques (chemically stained vs. digitally/virtually stained) and with a high degree of agreement between the techniques, without a clear preferable staining technique (virtual vs. histological). This digital or virtual staining of the tissue section sample 22 appears just like the tissue section sample 22 had undergone histochemical staining even though no such staining operation was conducted.

Figure 2:
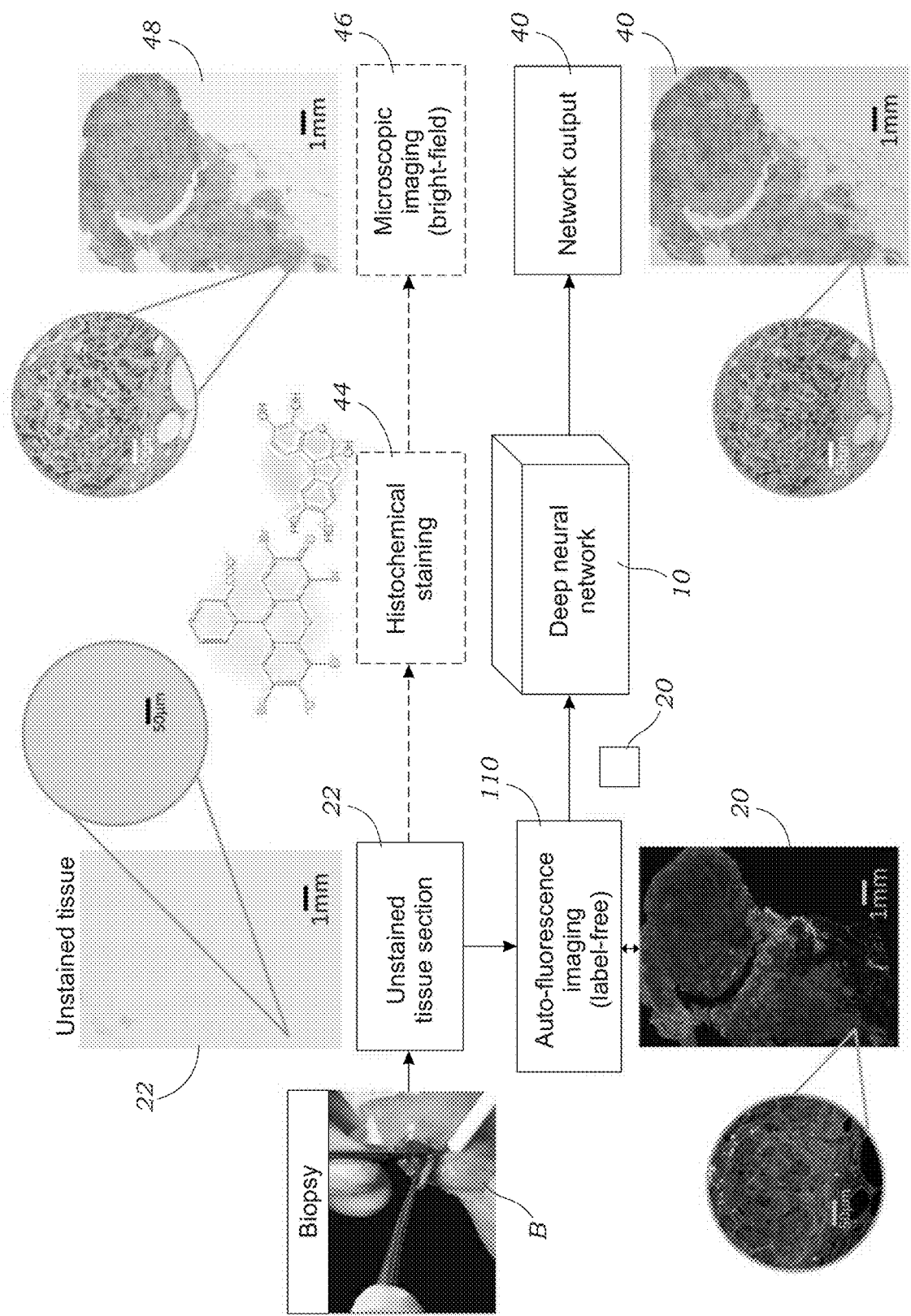
FIG. 2 illustrates a schematic representation of the deep learning-based digital/virtual histology staining operations using a fluorescence image of unstained tissue.

FIG. 2 schematically illustrates the operations involved in a typical fluorescent-based embodiment. As seen in FIG. 2, a sample 22 such as an unstained tissue section is obtained. This may be obtained from living tissue such as through a biopsy B or the like. The unstained tissue section sample 22 is then subject to fluorescent imaging using a fluorescence microscope 110 and generates a fluorescence image 20. This fluorescence image 20 is then input to a trained, deep neural network 10 that then promptly outputs a digitally stained image 40 of the tissue section sample 22. This digitally stained image 40 closely resembles the appearance of a brightfield image of the same tissue section sample 22 had the actual tissue section sample 22 be subject to histochemical staining. FIG. 2 illustrates (using dashed arrows) the conventional process whereby the tissue section sample 22 is subject to histochemical staining 44 followed by conventional brightfield microscopic imaging 46 to generate a conventional brightfield image 48 of the stained tissue section sample 22. As seen in FIG. 2, the digitally stained image 40 closely resembles the actual chemically stained image 48. Similar resolution and color profiles are obtained using the digital staining platform described herein. This digitally stained image 40 may, as illustrated in FIG. 1, be shown or displayed on a computer monitor 106 but it should be appreciated the digitally stained image 40 may be displayed on any suitable display (e.g., computer monitor, tablet computer, mobile computing device, mobile phone, etc.). A GUI may be displayed on the computer monitor 106 so that the user may view and optionally interact with the digitally stained image 40 (e.g., zoom, cut, highlight, mark, adjust exposure, and the like).

Experimental—Digital Staining of Label Free Tissue Using Auto-Fluorescence

Virtual Staining of Tissue Samples

The system 2 and methods described herein was tested and demonstrated using different combinations of tissue section samples 22 and stains. Following the training of a CNN-based deep neural network 10 its inference was blindly tested by feeding it with the auto-fluorescence images 20 of label-free tissue sections 22 that did not overlap with the images that were used in the training or validation sets. FIGS. 4A-4H illustrates the results for a salivary gland tissue section, which was digitally/virtually stained to match H&E stained brightfield images 48 (i.e., the ground truth images) of the same sample 22. These results demonstrate the capability of the system 2 to transform a fluorescence image 20 of a label-free tissue section 22 into a brightfield equivalent image 40, showing the correct color scheme that is expected from an H&E stained tissue, containing various constituents such as epithelioid cells, cell nuclei, nucleoli, stroma, and collagen. Evaluation of both FIGS. 3C and 3D show the H&E stains demonstrate a small island of infiltrating tumor cells within subcutaneous fibroadipose tissue. Note the nuclear detail, including distinction of nucleoli (arrow) and chromatin texture, is clearly appreciated in both panels. Similarly, in FIGS. 3G and 3H, the H&E stains demonstrate infiltrating squamous cell carcinoma. The desmoplastic reaction with edematous myxoid change (asterisk) in the adjacent stroma is clearly identifiable in both stains.

Next, the deep network 10 was trained to digitally/virtually stain other tissue types with two different stains, i.e., the Jones methenamine silver stain (kidney) and the Masson's Trichrome stain (liver and lung). FIGS. 4A-4H and 5A-5P summarize the results for deep learning-based digital/virtual staining of these tissue sections 22, which very well match to the brightfield images 48 of the same samples 22, captured after the histochemical staining process. These results illustrate that the trained deep neural network 10 is capable of inferring the staining patterns of different types of histology stains used for different tissue types, from a single fluorescence image 20 of a label-free specimen (i.e., without any histochemical stains). With the same overall conclusion as in FIGS. 3A-3H, it was also confirmed by a pathologist that the neural network output images FIGS. 4C and 5G correctly reveal the histological features corresponding to hepatocytes, sinusoidal spaces, collagen and fat droplets (FIG. 5G), consistent with the way that they appear in the brightfield images 48 of the same tissue samples 22, captured after the chemical staining (FIGS. 5D and 5H). Similarly, it was also confirmed by the same expert that the deep neural network output images 40 reported in FIGS. 5K and 5O (lung) reveal consistently stained histological features corresponding to vessels, collagen and alveolar spaces as they appear in the brightfield images 48 of the same tissue sample 22 imaged after the chemical staining (FIGS. 6L and 6P).

The digitally/virtually-stained output images 40 from the trained, deep neural network 10 were compared to the standard histochemical staining images 48 for diagnosing multiple types of conditions on multiple types of tissues, which were either Formalin-Fixed Paraffin-Embedded (FFPE) or frozen sections. The results are summarized in Table 1 below. The analysis of fifteen (15) tissue sections by four board certified pathologists (who were not aware of the virtual staining technique) demonstrated 100% non-major discordance, defined as no clinically significant difference in diagnosis among professional observers. The "time to diagnosis" varied considerably among observers, from an average of 10 seconds-per-image for observer 2 to 276 seconds-per-image for observer 3. However, the intra-observer variability was very minor and tended towards shorter time to diagnosis with the virtually-stained slide images 40 for all the observers except observer 2 which was equal, i.e., ~10 seconds-per-image for both the virtual slide image 40 and the histology stained slide image 48. These indicate very similar diagnostic utility between the two image modalities.

TABLE 1

| Serial number | Tissue, fixation, type of stain | Pathologist # | Histochemically/ Virtually stained | Diagnosis | Time to diagnose |
|---|---|---|---|---|---|
| 1 | Ovary, Frozen section, H&E | 1 | VS | Adenocarcinoma | 30 sec |
|  |  | 2 | VS | Borderline serous tumor | 15 sec |
|  |  | 3 | HS | Mucinous adenocarcinoma | 10 min |
|  |  | 4 | HS | Adenocarcinoma, endometrioid | 2 min |
| 2 | Ovary, Frozen section, H&E | 1 | VS | Benign ovary | 10 sec |
|  |  | 2 | VS | Benign ovary | 10 sec |
|  |  | 3 | HS | Normal ovary with corpus luteal cyst | 15 min |
|  |  | 4 | HS | Normal | 1 min |
| 3 | Salivary Gland, FFPE, H&E | 1 | VS | Benign salivary glands with mild chronic inflammation | 10 sec |
|  |  | 2 | VS | Benign parotid tissue | 5 sec |
|  |  | 3 | HS | Normal salivary gland | 1 min |
|  |  | 4 | HS | No histopathologic abnormality | 1 min |

TABLE 1-continued

| Serial number | Tissue, fixation, type of stain | Pathologist # | Histochemically/ Virtually stained | Diagnosis | Time to diagnose |
|---|---|---|---|---|---|
| 4 | Salivary Gland, Frozen section, H&E | 1 | HS | Pleomorphic adenoma | 5 sec |
|  |  | 2 | HS | Pleomorphic adenoma | 5 sec |
|  |  | 3 | VS | Pleomorphic adenoma | 3 min |
|  |  | 4 | VS | Pleomorphic adenoma | 2 sec |
| 5 | Salivary Gland, FFPE, H&E | 1 | HS | Mucoepidermoid carcinoma, low grade | 5 sec |
|  |  | 2 | HS | Salivary duct carcinoma | 5 sec |
|  |  | 3 | VS | Mucoepidermoid carcinoma | 10 min |
|  |  | 4 | VS | Mucoepidermoid Carcinoma | 10 sec |
| 6 | Breast, FFPE, H&E | 1 | VS | Invasive ductal carcinoma and DCIS | 15 sec |
|  |  | 2 | VS | Ductal carcinoma | 10 sec |
|  |  | 3 | HS | Invasive ductal carcinoma with DCIS | 2 min |
|  |  | 4 | HS | Invasive carcinoma | 1 minute |
| 7 | Skin, FFPE, H&E | 1 | HS | Malignant melanoma | 30 sec |
|  |  | 2 | HS | melanoma | 30 sec |
|  |  | 3 | VS | Melanoma | 5 min |
|  |  | 4 | VS | Melanoma | 1 min |
| 8 | Prostate, FFPE, H&E | 1 | HS | Prostatic adenocarcinoma 3 + 4 | 1 min |
|  |  | 2 | HS | Prostatic adenocarcinoma 4 + 3 | 5 sec |
|  |  | 3 | VS | Prostatic adenocarcinoma, Gleason pattern 3 + 4 | 5 min |
|  |  | 4 | VS | HG-PIN with cribiforming vs carcinoma | 5 min |
| 9 | Liver, FFPE, Masson's trichrome | 1 | VS | Benign liver with mild steatosis | 10 sec |
|  |  | 2 | VS | Benign liver with steatosis | 5 sec |
|  |  | 3 | HS | Hepatosteatosis, predominantly macrovesicular | 3 min |
|  |  | 4 | HS | Minimal steatosis, no fibrosis | 5 min |
| 10 | Liver, FFPE, Masson's trichrome | 1 | HS | Benign liver with bridging fibrosis | 10 sec |
|  |  | 2 | HS | Benign liver, bridging fibrosis | 5 sec |
|  |  | 3 | VS | Moderate cirrhosis | 1 min |
|  |  | 4 | VS | Mild portal inflammation, focal bridging fibrosis (Stage 2-3) | 5 minutes |
| 11 | Salivary Gland, FFPE, H&E | 1 | VS | Carcinoma | 5 sec |
|  |  | 2 | VS | Intraductal ca | 20 sec |
|  |  | 3 | HS | Poorly differentiated carcinoma | 1 min |
|  |  | 4 | HS | Low-grade salivary gland neoplasm | 1 minute |
| 12 | Salivary Gland, FFPE, H&E | 1 | HS | Adenocarcinoma | 5 sec |
|  |  | 2 | HS | Salivary duct carcinoma | 5 sec |
|  |  | 3 | VS | Salivary duct carcinoma | 2 min |
|  |  | 4 | VS | Low-grade salivary gland neoplasm | 1 minute |
| 13 | Thyroid, FFPE, H&E | 1 | VS | Papillary thyroid carcinoma, tall cell type | 10 sec |
|  |  | 2 | VS | Papillary thyroid ca, tall cell | 20 sec |
|  |  | 3 | HS | Papillary thyroid carcinoma, tall cell variant | 5 min |
|  |  | 4 | HS | PTC | 10 sec |
| 14 | Thyroid, FFPE, H&E | 1 | HS | Papillary thyroid carcinoma | 5 sec |
|  |  | 2 | HS | Medullary ca | 5 sec |
|  |  | 3 | VS | Papillary thyroid carcinoma, oncocytic variant | 7 min |
|  |  | 4 | VS | PTC | 10 sec |
| 15 | Thyroid, FFPE, H&E | 1 | VS | Papillary thyroid carcinoma | 5 sec |
|  |  | 2 | VS | Papillary thyroid ca | 5 sec |
|  |  | 3 | HS | Papillary thyroid carcinoma | 1 min |
|  |  | 4 | HS | PTC | 10 sec |

Blind Evaluation of Staining Efficacy for Whole Slide Images (WSIs)

After evaluating the differences in tissue section and stains, the ability of the virtual staining system 2 was tested in the specialized staining histology workflow. In particular, the autofluorescence distribution of 15 label-free samples of liver tissue sections and 13 label-free tissue sections of kidney were imaged with a 20×/0.75NA objective lens. All liver and kidney tissue sections were obtained from different patients and included both small biopsies and larger resections. All the tissue sections were obtained from FFPE but not cover slipped. After the autofluorescence scanning, the tissue sections were histologically stained with Masson's Trichrome (4 µm liver tissue sections) and Jones' stain (2 µm kidney tissue sections). The WSIs were then divided into training and test sets. For the liver slides cohort, 7 WSIs were used for training the virtual staining algorithm and 8 WSIs were used for blind testing; for the kidney slides cohort, 6 WSIs were used for training the algorithm and 7 WSIs were used for testing. The study pathologists were blinded to the staining techniques for each WSI and were asked to apply a 1-4 number grade for the quality of the different stains: 4=perfect, 3=very good, 2=acceptable, 1=unacceptable. Secondly, the study pathologists applied the same score scale (1-4) for specific features: nuclear detail (ND), cytoplasmic detail (CD) and extracellular fibrosis (EF), for liver only. These results are summarized in Table 2 (Liver) and Table 3 (Kidney) below (winner is bolded). The data indicates that the pathologists were able to recognize histopathologic features with both staining techniques and with a high degree of agreement between the techniques, without a clear preferable staining technique (virtual vs. histological).

TABLE 2

| Tis. # | Pathologist 1 | | | | Pathologist 2 | | | | Pathologist 3 | | | | Average | | | |
|---|---|---|---|---|---|---|---|---|---|---|---|---|---|---|---|---|
| | ND | CD | EF | SQ | ND | CD | EF | SQ | ND | CD | EF | SQ | ND | CD | EF | SQ |
| 1-HS | 3 | 2 | 1 | 1 | 4 | 4 | 3 | 4 | 1 | 1 | 1 | 3 | 2.67 | 2.33 | 1.67 | 2.67 |
| 1-VS | 3 | 3 | 3 | 3 | 3 | 3 | 2 | 3 | 2 | 2 | 3 | 3 | 2.67 | 2.67 | 2.67 | 3.00 |
| 2-HS | 3 | 2 | 4 | 4 | 4 | 4 | 3 | 4 | 1 | 2 | 2 | 2 | 2.67 | 2.67 | 3.00 | 3.33 |
| 2-VS | 3 | 3 | 4 | 4 | 4 | 3 | 3 | 3 | 2 | 2 | 3 | 3 | 3.00 | 2.67 | 3.33 | 3.33 |
| 3-HS | 3 | 3 | 2 | 2 | 3 | 3 | 4 | 3 | 1 | 1 | 1 | 1 | 2.33 | 2.33 | 2.33 | 2.00 |
| 3-VS | 3 | 2 | 1 | 1 | 3 | 3 | 1 | 4 | 1 | 1 | 1 | 1 | 2.33 | 2.00 | 1.00 | 2.00 |
| 4-HS | 3 | 2 | 4 | 4 | 3 | 4 | 4 | 4 | 1 | 2 | 1 | 2 | 2.33 | 2.67 | 3.00 | 3.33 |
| 4-VS | 3 | 3 | 4 | 4 | 3 | 3 | 4 | 4 | 2 | 2 | 3 | 3 | 3.00 | 2.67 | 3.67 | 3.67 |
| 5-HS | 3 | 3 | 4 | 4 | 3 | 3 | 2 | 1 | 1 | 3 | 2 | 2 | 2.33 | 3.00 | 2.67 | 2.33 |
| 5-VS | 3 | 2 | 3 | 3 | 3 | 3 | 4 | 2 | 2 | 1 | 3 | 3 | 2.67 | 2.00 | 3.33 | 2.67 |
| 6-HS | 3 | 2 | 3 | 3 | 4 | 4 | 4 | 3 | 2 | 2 | 2 | 2 | 3.00 | 2.67 | 3.00 | 2.67 |
| 6-VS | 3 | 3 | 4 | 3 | 4 | 3 | 4 | 3 | 1 | 1 | 1 | 1 | 2.67 | 2.33 | 3.00 | 2.33 |
| 7-HS | 3 | 3 | 4 | 4 | 3 | 4 | 4 | 3 | 2 | 1 | 2 | 2 | 2.67 | 2.67 | 3.33 | 3.00 |
| 7-VS | 3 | 2 | 3 | 3 | 4 | 4 | 4 | 3 | 2 | 2 | 3 | 3 | 3.00 | 2.67 | 3.33 | 3.00 |
| 8-HS | 3 | 3 | 4 | 4 | 4 | 4 | 4 | 3 | 1 | 1 | 1 | 1 | 2.67 | 2.67 | 3.00 | 2.67 |
| 8-VS | 3 | 2 | 4 | 4 | 4 | 3 | 4 | 4 | 2 | 2 | 3 | 2 | 3.00 | 2.33 | 3.67 | 3.33 |

TABLE 3

| Tissue # | Pathologist 1 | | | Pathologist 2 | | | Pathologist 3 | | | Average | | |
|---|---|---|---|---|---|---|---|---|---|---|---|---|
| | ND | CD | SQ | ND | CD | SQ | ND | CD | SQ | ND | CD | SQ |
| 1-HS | 3 | 3 | 3 | 2 | 2 | 4 | 2 | 2 | 2 | 2.33 | 2.33 | 3.00 |
| 1-VS | 2 | 3 | 3 | 3 | 3 | 4 | 3 | 3 | 3 | 2.67 | 3.00 | 3.33 |
| 2-HS | 2 | 4 | 4 | 3 | 3 | 2 | 1 | 1 | 2 | 2.00 | 2.67 | 2.67 |
| 2-VS | 2 | 3 | 4 | 3 | 3 | 3 | 1 | 2 | 3 | 2.00 | 2.67 | 3.33 |
| 3-HS | 2 | 3 | 3 | 3 | 3 | 2 | 2 | 3 | 4 | 2.33 | 3.00 | 3.00 |
| 3-VS | 2 | 3 | 3 | 3 | 3 | 3 | 1 | 2 | 3 | 2.00 | 2.67 | 3.00 |
| 4-HS | 3 | 3 | 3 | 2 | 2 | 2 | 1 | 2 | 3 | 2.00 | 2.33 | 2.67 |
| 4-VS | 3 | 3 | 3 | 2 | 2 | 3 | 1 | 2 | 2 | 2.00 | 2.33 | 2.67 |
| 5-HS | 3 | 3 | 2 | 3 | 3 | 1 | 3 | 3 | 3 | 3.00 | 3.00 | 2.00 |
| 5-VS | 3 | 3 | 2 | 4 | 3 | 4 | 3 | 3 | 4 | 3.33 | 3.00 | 3.33 |
| 6-HS | 2 | 3 | 3 | 3 | 3 | 1 | 2 | 2 | 2 | 2.33 | 2.67 | 2.00 |
| 6-VS | 2 | 2 | 3 | 2 | 2 | 2 | 2 | 2 | 2 | 2.00 | 2.00 | 2.33 |
| 7-HS | 3 | 3 | 2 | 3 | 2 | 2 | 3 | 3 | 3 | 3.00 | 2.67 | 2.33 |
| 7-VS | 3 | 3 | 2 | 4 | 3 | 1 | 3 | 2 | 3 | 3.33 | 2.67 | 2.00 |

TABLE 4

| Virtual histological staining using a deep network | Number of test images | SSIM | | Y difference (%) | | Cb difference (%) | | Cr difference (%) | |
|---|---|---|---|---|---|---|---|---|---|
| | | mean | std | mean | std | mean | std | mean | std |
| Salivary gland (H&E) | 10 | 0.826 | 0.059 | 11.5 | 9.0 | 2.5 | 2.4 | 2.5 | 2.5 |
| Thyroid (H&E) | 30 | 0.789 | 0.044 | 10.1 | 7.9 | 3.4 | 2.7 | 2.8 | 2.7 |
| Thyroid (H&E, transfer learning) | 30 | 0.839 | 0.029 | 14.0 | 8.4 | 2.4 | 2.2 | 2.6 | 2.6 |
| Liver (Masson's Trichrome) | 30 | 0.847 | 0.023 | 11.0 | 8.9 | 3.1 | 2.7 | 4.0 | 3.5 |
| Lung (Masson's Trichrome) | 48 | 0.776 | 0.039 | 15.9 | 11.7 | 4.0 | 3.6 | 5.3 | 4.9 |
| Kidney (Jones Stain) | 30 | 0.841 | 0.021 | 16.1 | 10.4 | 2.5 | 2.2 | 3.6 | 3.4 |

Quantification of the Network Output Image Quality

Next, beyond the visual comparison provided in FIGS. 3A-3H, 4A-4H, 5A-5P, the results of the trained deep neural network 10 were quantified by first calculating the pixel-level differences between the brightfield images 48 of the chemically stained samples 22 and the digitally/virtually stained images 40 that are synthesized using the deep neural network 10 without the use of any labels/stains. Table 4 below summarizes this comparison for different combinations of tissue types and stains, using the YCbCr color space, where the chroma components Cb and Cr entirely define the color, and Y defines the brightness component of the image. The results of this comparison reveal that the average difference between these two sets of images is <~5% and <~16%, for the chroma (Cb, Cr) and brightness (Y) channels, respectively. Next, a second metric was used to further quantify the comparison, i.e., the structural similarity index (SSIM), which is in general used to predict the score that a human observer will give for an image, in comparison to a reference image (Equation 8 herein). SSIM ranges between 0 and 1, where 1 defines the score for identical images. The results of this SSIM quantification are also summarized in Table 4, which very well illustrates the strong structural similarity between the network output images 40 and the brightfield images 48 of the chemically stained samples.

One should note that the brightfield images 48 of the chemically stained tissue samples 22 in fact do not provide the true gold standard for this specific SSIM and YCbCr analysis of the network output images 40, because there are uncontrolled variations and structural changes that the tissue undergoes during the histochemical staining process and related dehydration and clearing steps. Another variation that was noticed for some of the images was that the automated microscope scanning software selected different auto-focusing planes for the two imaging modalities. All these variations create some challenges for the absolute quantitative comparison of the two sets of images (i.e., the network output 40 for a label-free tissue vs. the brightfield image 48 of the same tissue after the histological staining process).

Staining Standardization

An interesting by-product of the digital/virtual staining system 2 can be staining standardization. In other words, the trained deep neural network 10 converges to a "common stain" colorization scheme whereby the variation in the histologically stained tissue images 48 is higher than that of the virtually stained tissue images 40. The colorization of the virtual stain is solely the result of its training (i.e., the gold standard histological staining used during the training phase) and can be further adjusted based on the preferences of pathologists, by retraining the network with a new stain colorization. Such "improved" training can be created from scratch or accelerated through transfer learning. This potential staining standardization using deep learning can remedy the negative effects of human-to-human variations at different stages of the sample preparation, create a common ground among different clinical laboratories, enhance the diagnostic workflow for clinicians as well as assist the development of new algorithms such as automatic tissue metastasis detection or grading of different types of cancer, among others.

Transfer Learning to Other Tissue-Stain Combinations

Using the concept of transfer learning, the training procedure for new tissue and/or stain types can converge much faster, while also reaching an improved performance, i.e., a better local minimum in the training cost/loss function. This means, a pre-learnt CNN model deep neural network 10, from a different tissue-stain combination, can be used to initialize the deep neural network 10 to statistically learn virtual staining of a new combination. FIGS. 6A-6C shows the favorable attributes of such an approach: a new deep neural network 10 was trained to virtually stain the auto-fluorescence images 20 of unstained thyroid tissue sections, and it was initialized using the weights and biases of another deep neural network 10 that was previously trained for H&E virtual staining of the salivary gland. The evolution of the loss metric as a function of the number of iterations used in the training phase clearly demonstrates that the new thyroid deep network 10 rapidly converges to a lower minimum in comparison to the same network architecture which was trained from scratch, using random initialization as seen in FIG. 6A. FIG. 6B compares the output images 40 of this thyroid network 10 at different stages of its learning process, which further illustrates the impact of transfer learning to rapidly adapt the presented approach to new tissue/stain combinations. The network output images 40, after the training phase with e.g., >6,000 iterations, reveal that cell nuclei show irregular contours, nuclear grooves, and chromatin pallor, suggestive of papillary thyroid carcinoma; cells also show mild to moderate amounts of eosinophilic granular cytoplasm and the fibrovascular core at the network output image shows increased inflammatory cells including lymphocytes and plasma cells. FIG. 6C illustrates the corresponding H&E chemically stained brightfield image 48.

Using Multiple Fluorescent Channels at Different Resolutions

Figures 7A, 7B, 7C:
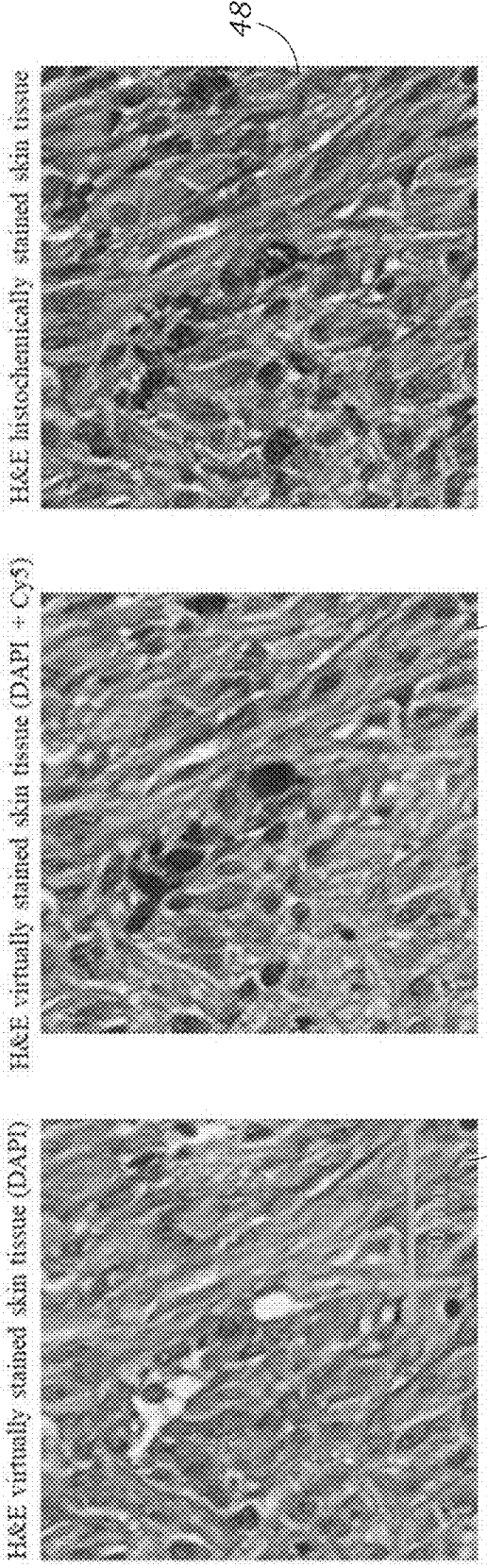
FIG. 7A illustrates the virtual staining (H&E stain) of skin tissue using the DAPI channel only.
FIG. 7B illustrates the virtual staining (H&E stain) of skin tissue using the DAPI and Cy5 channels. Cy5 refers to a far-red-fluorescent label cyanine dye used to label biomolecules.
FIG. 7C illustrates the corresponding histologically stained (i.e., chemically stained with H&E) tissue.

The method of using the trained, deep neural network 10 can be combined with other excitation wavelengths and/or imaging modalities in order to enhance its inference performance for different tissue constituents. For example, melanin detection on a skin tissue section sample using virtual H&E staining was tried. However, melanin was not clearly identified in the output of the network, as it presents a weak auto-fluorescent signal at DAPI excitation/emission wavelengths measured in the experimental system described herein. One potential method to increase the autofluorescence of melanin is to image the samples while they are in an oxidizing solution. However, a more practical alternative was used where an additional autofluorescence channel was employed, originating from e.g., Cy5 filter (excitation 628 nm/emission 692 nm) such that the melanin signal can be enhanced and accurately inferred in the trained, deep neural network 10. By training the network 10 using both the DAPI and Cy5 autofluorescence channels, the trained, deep neural network 10 was able to successfully determine where melanin occurs in the sample, as illustrated in FIGS. 7A-7C. In contrast, when only the DAPI channel was used (FIG. 7A), the network 10 was unable to determine the areas that contain melanin (the areas appear white). Stated differently, the additional autofluorescence information from the Cy5 channel was used by the network 10 to distinguish melanin from the background tissue. For the results that are shown in FIGS. 7A-7C, the images 20 were acquired using a lower resolution objective lens (10×/0.45NA) for the Cy5 channel, to supplement the high-resolution DAPI scan (20×/0.75NA), as it was hypothesized that most necessary information is found in the high-resolution DAPI scan and the additional information (for example, the melanin presence) can be encoded with the lower resolution scan. In this manner, two different channels were used with one of the channels being used at a lower resolution to identify the melanin. This may require multiple scanning passes of the sample 22 with the fluorescent microscope 110. In yet another multi-channel embodiment, multiple images 20 may be fed to the trained, deep neural network 10. This may include, for example, raw fluorescent images in combination with one or more images that have undergone linear or non-linear image pre-processing such as contrast enhancement, contrast reversal, and image filtering.

The system 2 and methods described herein show the ability to digitally/virtually stain label-free tissue sections 22, using a supervised deep learning technique that uses a single fluorescence image 20 of the sample as input, captured by a standard fluorescence microscope 110 and filter set (in other embodiments multiple fluorescence images 20 are input when multiple fluorescence channels are used). This statistical learning-based method has the potential to restructure the clinical workflow in histopathology and can benefit from various imaging modalities such as fluorescence microscopy, non-linear microscopy, holographic microscopy, stimulated Raman scattering microscopy, and optical coherence tomography, among others, to potentially provide a digital alternative to the standard practice of histochemical staining of tissue samples 22. Here, the method was demonstrated using fixed unstained tissue samples 22 to provide a meaningful comparison to chemically stained tissue samples, which is essential to train the deep neural network 10 as well as to blindly test the performance of the network output against the clinically-approved method. However, the presented deep learning-based approach is broadly applicable to different types and states of a sample 22 including un-sectioned, fresh tissue samples (e.g., following a biopsy procedure) without the use of any labels or stains. Following its training, the deep neural network 10 can be used to digitally/virtually stain the images of label-free fresh tissue samples 22, acquired using e.g., UV or deep UV excitation or even nonlinear microscopy modalities. For example, Raman microscopy can provide very rich label-free biochemical signatures that can further enhance the effectiveness of the virtual staining that the neural network learns.

An important part of the training process involves matching the fluorescence images 20 of label-free tissue samples 22 and their corresponding brightfield images 48 after the histochemical staining process (i.e., chemically stained images). One should note that during the staining process and related steps, some tissue constitutes can be lost or deformed in a way that will mislead the loss/cost function in the training phase. This, however, is only a training and validation related challenge and does not pose any limitations on the practice of a well-trained deep neural network 10 for virtual staining of label-free tissue samples 22. To ensure the quality of the training and validation phase and minimize the impact of this challenge on the network's performance, a threshold was established for an acceptable correlation value between the two sets of images (i.e., before and after the histochemical staining process) and eliminated the non-matching image pairs from the training/validation set to make sure that the deep neural network 10 learns the real signal, not the perturbations to the tissue morphology due to the chemical staining process. In fact, this process of cleaning the training/validation image data can be done iteratively: one can start with a rough elimination of the obviously altered samples and accordingly converge on a neural network 10 that is trained. After this initial training phase, the output images 40 of each sample in the available image set can be screened against their corresponding brightfield images 48 to set a more refined threshold to reject some additional images and further clean the training/validation image set. With a few iterations of this process, one can, not only further refine the image set, but also improve the performance of the final trained deep neural network 10.

The methodology described above will mitigate some of the training challenges due to random loss of some tissue features after the histological staining process. In fact, this highlights another motivation to skip the laborious and costly procedures that are involved in histochemical staining as it will be easier to preserve the local tissue histology in a label-free method, without the need for an expert to handle some of the delicate procedures of the staining process, which sometimes also requires observing the tissue under a microscope.

Using a PC desktop, the training phase of the deep neural network 10 takes a considerable amount of time (e.g., ~13 hours for the salivary gland network). However, this entire process can be significantly accelerated by using dedicated computer hardware, based on GPUs. Furthermore, as already emphasized in FIGS. 6A-6C, transfer learning provides a "warm start" to the training phase of a new tissue/stain combination, making the entire process significantly faster. Once the deep neural network 10 has been trained, the digital/virtual staining of a sample image 40 is performed in a single, non-iterative manner, which does not require a trial-and-error approach or any parameter tuning to achieve the optimal result. Based on its feed-forward and non-iterative architecture, the deep neural network 10 rapidly outputs a virtually stained image in less than one second (e.g., 0.59 sec, corresponding to a sample field-of-view of ~0.33 mm×0.33 mm). With further GPU-based acceleration, it has the potential to achieve real-time or near real-time performance in outputting digitally/virtually stained images 40 which might especially be useful in the operating room or for in vivo imaging applications.

The digital/virtual staining procedure that is implemented is based on training a separate CNN deep neural network 10 for each tissue/stain combination. If one feeds a CNN-based deep neural network 10 with the auto-fluorescence images 20 having different tissue/stain combinations, it will not perform as desired. This, however, is not a limitation because for histology applications, the tissue type and stain type are pre-determined for each sample 22 of interest, and therefore, a specific CNN selection for creating the digitally/virtually stained image 40 from an auto-fluorescence image 20 of the unlabeled sample 22 does not require an additional information or resource. Of course, a more general CNN model can be learnt for multiple tissue/stain combinations by e.g., increasing the number of trained parameters in the model, at the cost of a possible increase in the training and inference times. Another avenue is the potential of the system 2 and method to perform multiple virtual stains on the same unlabeled tissue type.

A significant advantage of the system 2 is that it is quite flexible. It can accommodate feedback to statistically mend its performance if a diagnostic failure is detected through a clinical comparison, by accordingly penalizing such failures as they are caught. This iterative training and transfer learning cycle, based on clinical evaluations of the performance of the network output, will help optimize the robustness and clinical impact of the presented approach. Finally, this method and system 2 may be used for micro-guiding molecular analysis at the unstained tissue level, by locally identifying regions of interest based on virtual staining, and using this information to guide subsequent analysis of the tissue for e.g., micro-immunohistochemistry or sequencing. This type of virtual micro-guidance on an unlabeled tissue sample can facilitate high-throughput identification of subtypes of diseases, also helping the development of customized therapies for patients.

Sample Preparation

Formalin-fixed paraffin-embedded 2 µm thick tissue sections were deparaffinized using Xylene and mounted on a standard glass slide using Cytoseal™ (Thermo-Fisher Scientific, Waltham, MA USA), followed by placing a coverslip (Fisherfinest™, 24×50-1, Fisher Scientific, Pittsburgh, PA USA). Following the initial auto-fluorescence imaging process (using a DAPI excitation and emission filter set) of the unlabeled tissue sample, the slide was then put into Xylene for approximately 48 hours or until the coverslip can be removed without damaging the tissue. Once the coverslip is removed the slide was dipped (approximately 30 dips) in absolute alcohol, 95% alcohol and then washed in D.I. water for ~1 min. This step was followed by the corresponding staining procedures, used for H&E, Masson's Trichrome or Jones stains. This tissue processing path is only used for the training and validation of the approach and is not needed after the network has been trained. To test the system and method, different tissue and stain combinations were used: the salivary gland and thyroid tissue sections were stained with H&E, kidney tissue sections were stained with Jones stain, while the liver and lung tissue sections were stained with Masson's trichrome.

In the WSI study, the FFPE 2-4 µm thick tissue sections were not cover slipped during the autofluorescence imaging stage. Following the autofluorescence imaging, the tissue samples were histologically stained as described above (Masson's Trichrome for the liver and Jones for the kidney tissue sections). The unstained frozen samples were prepared by embedding the tissue section in O.C.T. (Tissue Tek, SAKURA FINETEK USA INC) and dipped in 2-Methylbutane with dry ice. The frozen section was then cut to 4 µm sections and was put in a freezer until it was imaged. Following the imaging process, the tissue section was washed with 70% alcohol, H&E stained and cover slipped. The samples were obtained from the Translational Pathology Core Laboratory (TPCL) and were prepared by the Histology Lab at UCLA. The kidney tissue sections of diabetic and non-diabetic patients were obtained under IRB 18-001029 (UCLA). All the samples were obtained after de-identification of the patient related information, and were prepared from existing specimen. Therefore, this work did not interfere with standard practices of care or sample collection procedures.

Data Acquisition

The label-free tissue auto-fluorescence images 20 were captured using a conventional fluorescence microscope 110 (1X83, Olympus Corporation, Tokyo, Japan) equipped with a motorized stage, where the image acquisition process was controlled by MetaMorph® microscope automation software (Molecular Devices, LLC). The unstained tissue samples were excited with near UV light and imaged using a DAPI filter cube (OSFI3-DAPI-5060C, excitation wavelength 377 nm/50 nm bandwidth, emission wavelength 447 nm/60 nm bandwidth) with a 40×/0.95NA objective lens (Olympus UPLSAPO 40×2/0.95NA, WD0.18) or 20×/0.75NA objective lens (Olympus UPLSAPO 20×/0.75NA, WD0.65). For the melanin inference, the autofluorescence images of the samples were additionally acquired using a Cy5 filter cube (CY5-4040C-OFX, excitation wavelength 628 nm/40 nm bandwidth, emission wavelength 692 nm/40 nm bandwidth) with a 10×/0.4NA objective lens (Olympus UPLSAPO10X2). Each auto-fluorescence image was captured with a scientific CMOS sensor (ORCA-flash4.0 v2, Hamamatsu Photonics K.K., Shizuoka Prefecture, Japan) with an exposure time of ~500 ms. The brightfield images 48 (used for the training and validation) were acquired using a slide scanner microscope (Aperio AT, Leica Biosystems) using a 20×/0.75NA objective (Plan Apo), equipped with a 2× magnification adapter.

Image Pre-Processing and Alignment

Figure 8:
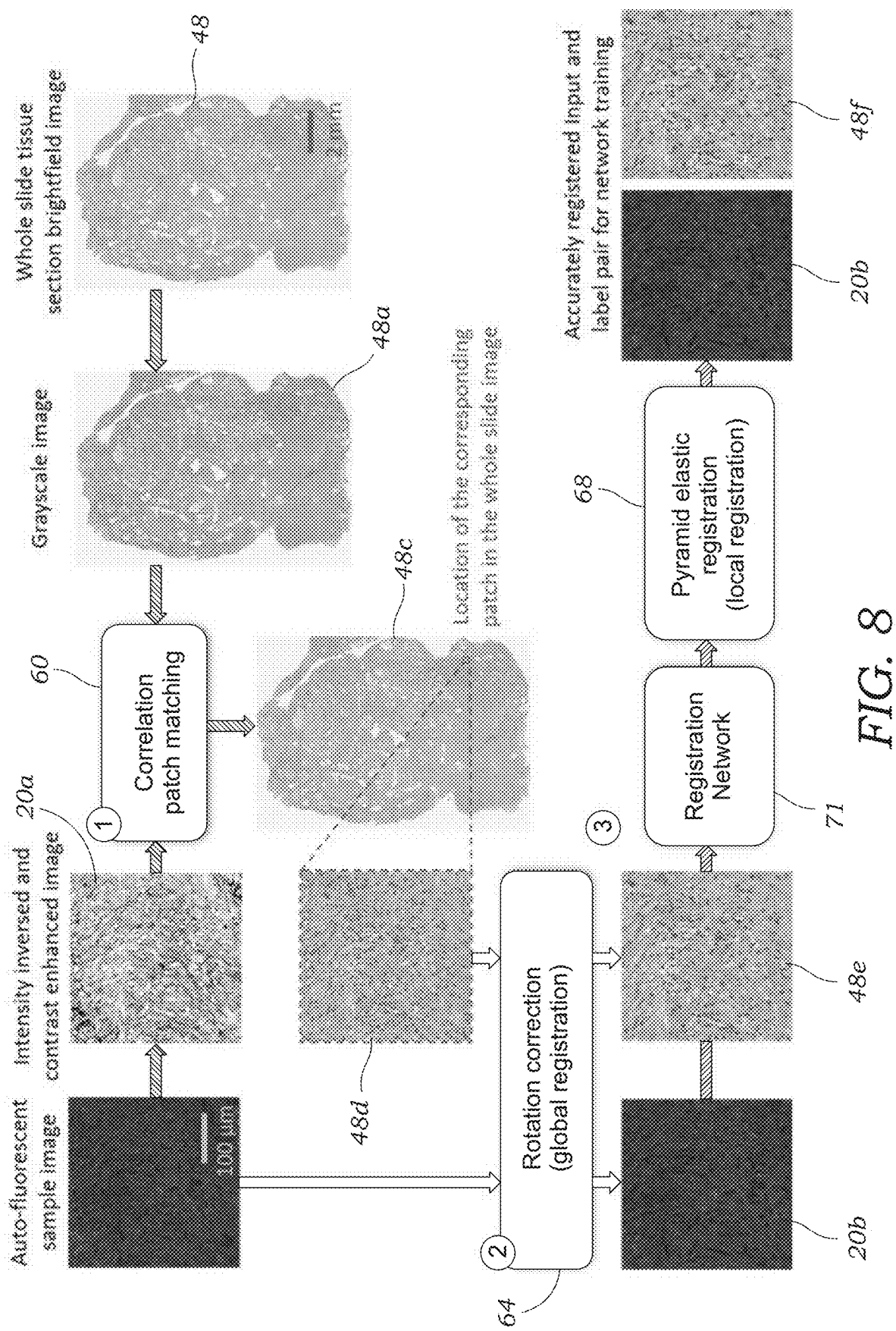
FIG. 8 illustrates the field-of-view matching and registration process of the auto-fluorescence images of unstained tissue samples with respect to the brightfield images of the same samples, after the chemical staining process.

Since the deep neural network 10 aims to learn a statistical transformation between an auto-fluorescence image 20 of a chemically unstained tissue sample 22 and a brightfield image 48 of the same tissue sample 22 after the histochemical staining, it is important to accurately match the FOV of the input and target images (i.e., unstained auto-fluorescence image 20 and the stained bright-filed image 48). An overall scheme describing the global and local image registration process is described in FIG. 8 which was implemented in MATLAB (The MathWorks Inc., Natick, MA, USA). The first step in this process is to find candidate features for matching unstained auto-fluorescence images and chemically stained brightfield images. For this, each auto-fluorescence image 20 (2048×2048 pixels) is down-sampled to match the effective pixel size of the brightfield microscope images. This results in a 1351×1351-pixel unstained auto-fluorescent tissue image, which is contrast enhanced by saturating the bottom 1% and the top 1% of all the pixel values, and contrast reversed (image 20a in FIG. 8) to better represent the color map of the grayscale converted whole slide image. Then, a correlation patch process 60 is performed in which a normalized correlation score matrix is calculated by correlating each one of the 1351×1351-pixel patches with the corresponding patch of the same size, extracted from the whole slide gray-scale image 48a. The entry in this matrix with the highest score represents the most likely matched FOV between the two imaging modalities. Using this information (which defines a pair of coordinates), the matched FOV of the original whole slide brightfield image 48 is cropped 48c to create target images 48d. Following this FOV matching procedure 60, the auto-fluorescence 20 and brightfield microscope images 48 are coarsely matched. However, they are still not accurately registered at the individual pixel-level, due to the slight mismatch in the sample placement at the two different microscopic imaging experiments (auto-fluorescence, followed by brightfield), which randomly causes a slight rotation angle (e.g., ~1-2 degrees) between the input and target images of the same sample.

The second part of the input-target matching process involves a global registration step 64, which corrects for this slight rotation angle between the auto-fluorescence and brightfield images. This is done by extracting feature vectors (descriptors) and their corresponding locations from the image pairs, and matching the features by using the extracted descriptors. Then, a transformation matrix corresponding to the matched pairs is found using the M-estimator Sample Consensus (MSAC) algorithm, which is a variant of the Random Sample Consensus (RANSAC) algorithm. Finally, the angle-corrected image 48e is obtained by applying this transformation matrix to the original brightfield microscope image patch 48d. Following the application of this rotation, the images 20b, 48e are further cropped by 100 pixels (50 pixels on each side) to accommodate for undefined pixel values at the image borders, due to the rotation angle correction.

Finally, for the local feature registration operation 68, an elastic image registration, which matches the local features of both sets of images (auto-fluorescence 20b vs. brightfield 48e), by hierarchically matching the corresponding blocks, from large to small. A neural network 71 is used to learn the transformation between the roughly matched images. This network 71 uses the same structure as the network 10 in FIG. 10. A low number of iterations is used so that the network 71 only learns the accurate color mapping, and not any spatial transformations between the input and label images. The calculated transformation map from this step is finally applied to each brightfield image patch 48e. At the end of these registration steps 60, 64, 68, the auto-fluorescence image patches 20b and their corresponding brightfield tissue image patches 48f are accurately matched to each other and can be used as input and label pairs for the training of the deep neural network 10, allowing the network to solely focus on and learn the problem of virtual histological staining.

For the 20× objective lens images (that were used for generating Table 2 and Table 3 data) a similar process was used. Instead of down-sampling the auto-fluorescence images 20, the bright-field microscope images 48 were down-sampled to 75.85% of their original size so that they match with the lower magnification images. Furthermore, to create whole slide images using these 20× images, additional shading correction and normalization techniques were applied. Before being fed into the network 71, each field-of-view was normalized by subtracting the mean value across the entire slide and dividing it by the standard deviation between pixel values. This normalizes the network input both within each slide as well as between slides. Finally, shading correction was applied to each image to account for the lower relative intensity measured at the edges of each field-of-view.

Deep Neural Network Architecture and Training

Figure 9:
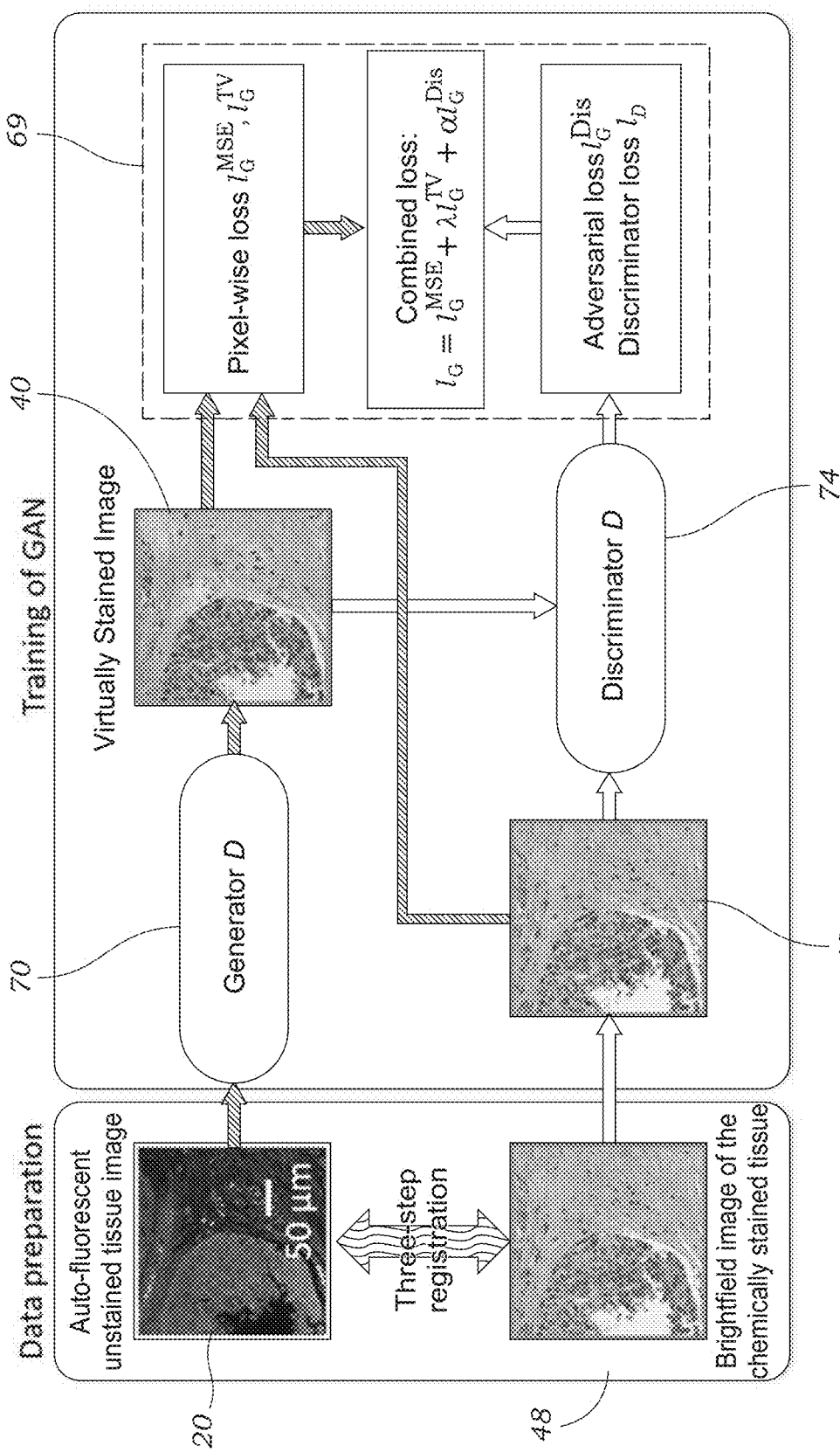
FIG. 9 schematically illustrates the training process of the virtual staining network using a GAN.
Figure 10:
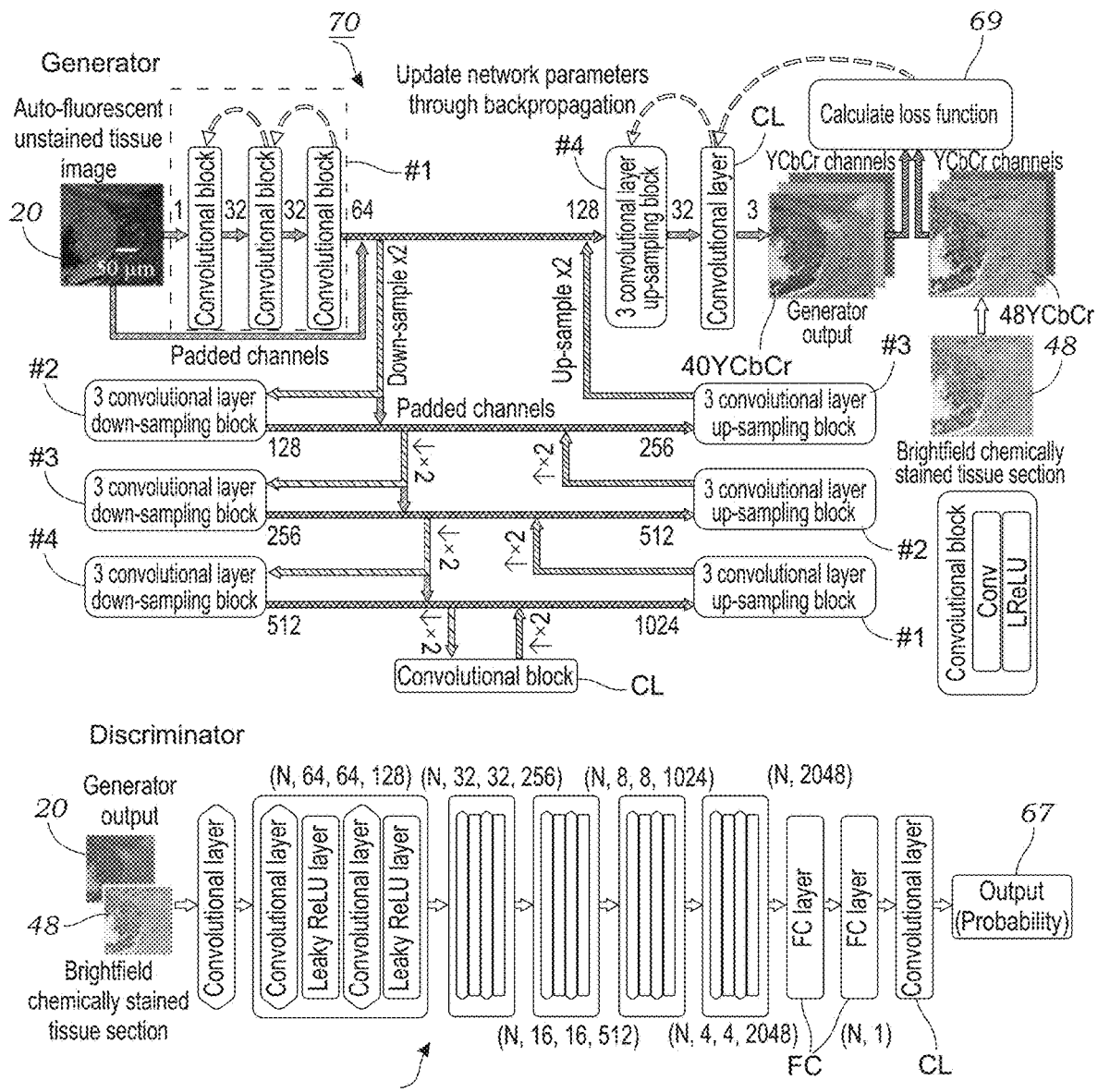
FIG. 10 illustrates the generative adversarial network (GAN) architecture for the generator and discriminator according to one embodiment.

In this work, a GAN architecture was used to learn the transformation from a label-free unstained auto-fluorescence input image 20 to the corresponding brightfield image 48 of the chemically stained sample. A standard convolutional neural network-based training learns to minimize a loss/cost function between the network's output and the target label. Thus, the choice of this loss function 69 (FIGS. 9 and 10) is a critical component of the deep network design. For instance, simply choosing an $l_2$-norm penalty as a cost function will tend to generate blurry results, as the network averages a weighted probability of all the plausible results; therefore, additional regularization terms are generally needed to guide the network to preserve the desired sharp sample features at the network's output. GANs avoid this problem by learning a criterion that aims to accurately classify if the deep network's output image is real or fake (i.e., correct in its virtual staining or wrong). This makes the output images that are inconsistent with the desired labels not to be tolerated, which makes the loss function to be adaptive to the data and the desired task at hand. To achieve this goal, the GAN training procedure involves training of two different networks, as shown in FIGS. 9 and 10: (i) a generator network 70, which in this case aims to learn the statistical transformation between the unstained auto-fluorescence input images 20 and the corresponding brightfield images 48 of the same samples 12, after the histological staining process; and (ii) a discriminator network 74 that learns how to discriminate between a true brightfield image of a stained tissue section and the generator network's output image. Ultimately, the desired result of this training process is a trained deep neural network 10, which transforms an unstained auto-fluorescence input image 20 into a digitally stained image 40 which will be indistinguishable from the stained brightfield image 48 of the same sample 22. For this task, the loss functions 69 of the generator 70 and discriminator 74 were defined as such:

$$\ell_{generator} = MSE\{z_{label}, z_{output}\} + \lambda \times TV\{z_{output}\} + \alpha \times (1 - D(z_{output}))^2$$

$$\ell_{discriminator} = D(z_{output})^2 + (1 - D(z_{label}))^2 \quad (1)$$

where D refers to the discriminator network output, $z_{label}$ denotes the brightfield image of the chemically stained tissue, $z_{output}$ denotes the output of the generator network. The generator loss function balances the pixel-wise mean squared error (MSE) of the generator network output image with respect to its label, the total variation (TV) operator of the output image, and the discriminator network prediction of the output image, using the regularization parameters ($\lambda$, $\alpha$) that are empirically set to different values, which accommodate for ~2% and ~20% of the pixel-wise MSE loss and the combined generator loss ($l_{generator}$), respectively. The TV operator of an image z is defined as:

$$TV(z) = \sum_p \sum_q \sqrt{(z_{p+1,q} - z_{p,q})^2 + (z_{p,q+1} - z_{p,q})^2} \quad (2)$$

where p, q are pixel indices. Based on Eq. (1), the discriminator attempts to minimize the output loss, while maximizing the probability of correctly classifying the real label (i.e., the brightfield image of the chemically stained tissue). Ideally, the discriminator network would aim to achieve $D(z_{label})=1$ and $D(z_{output})=0$, but if the generator is successfully trained by the GAN, $D(z_{output})$ will ideally converge to 0.5.

The generator deep neural network architecture 70 is detailed in FIG. 10. An input image 20 is processed by the network 70 in a multi-scale fashion, using down-sampling and up-sampling paths, helping the network to learn the virtual staining task at various different scales. The down-sampling path consists of four individual steps (four blocks #1, #2, #3, #4), with each step containing one residual block, each of which maps a feature map $x_k$ into feature map $x_{k+1}$:

$$x_{k+1} = x_k + LReLU[CONV_{k3}\{LReLU[CONV_{k2}\{LReLU[CONV_{k1}\{x_k\}]\}]\}] \quad (3)$$

where CONV{.} is the convolution operator (which includes the bias terms), k1, k2, and k3 denote the serial number of the convolution layers, and LReLU[.] is the non-linear activation function (i.e., a Leaky Rectified Linear Unit) that was used throughout the entire network, defined as:

$$LReLU(x) = \begin{cases} x & \text{for } x > 0 \\ 0.1x & \text{otherwise} \end{cases} \quad (4)$$

The number of the input channels for each level in the down-sampling path was set to: 1, 64, 128, 256, while the number of the output channels in the down-sampling path was set to: 64, 128, 256, 512. To avoid the dimension mismatch for each block, the feature map $x_k$ was zero-padded to match the number of the channels in $x_{k+1}$. The connection between each down-sampling level is a 2×2 average pooling layer with a stride of 2 pixels that down-samples the feature maps by a factor of 4 (2-fold for in each direction). Following the output of the fourth down-sampling block, another convolutional layer (CL) maintains the number of the feature maps as 512, before connecting it to the up-sampling path. The up-sampling path consists of four, symmetric, up-sampling steps (#1, #2, #3, #4), with each step containing one convolutional block. The convolutional block operation, which maps feature map $y_k$ into feature map $y_{k+1}$, is given by:

$$y_{k+1} = LReLU[CONV_{k6}\{LReLU[CONV_{k5}\{LReLU[CONV_{k4}\{CONCAT(x_{k+1}, US\{y_k\})\}]\}]\}] \quad (5)$$

where CONCAT(.) is the concatenation between two feature maps which merges the number of channels, US{.} is the up-sampling operator, and k4, k5, and k6, denote the serial number of the convolution layers. The number of the input channels for each level in the up-sampling path was set to 1024, 512, 256, 128 and the number of the output channels for each level in the up-sampling path was set to 256, 128, 64, 32, respectively. The last layer is a convolutional layer (CL) mapping 32 channels into 3 channels, represented by the YCbCr color map. Both the generator and the discriminator networks were trained with a patch size of 256×256 pixels.

The discriminator network, summarized in FIG. 10, receives three (3) input channels, corresponding to the YCbCr color space of an input image 40YCbCr, 48YCbCr. This input is then transformed into a 64-channel representation using a convolutional layer, which is followed by 5 blocks of the following operator:

$$z_{k+1} = LReLU[CONV_{k2}\{LReLU[CONV_{k1}\{z_k\}]\}] \quad (6)$$

where k1, k2, denote the serial number of the convolutional layer. The number of channels for each layer was 3, 64, 64, 128, 128, 256, 256, 512, 512, 1024, 1024, 2048. The next layer was an average pooling layer with a filter size that is equal to the patch size (256×256), which results in a vector with 2048 entries. The output of this average pooling layer is then fed into two fully connected layers (FC) with the following structure:

$$z_{k+1} = FC[LReLU[FC\{z_k\}]] \quad (7)$$

where FC represents the fully connected layer, with learnable weights and biases. The first fully connected layer outputs a vector with 2048 entries, while the second one outputs a scalar value. This scalar value is used as an input to a sigmoid activation function $D(z)=1/(1+\exp(-z))$ which calculates the probability (between 0 and 1) of the discriminator network input to be real/genuine or fake, i.e., ideally $D(z_{label})=1$ as illustrated by output 67 in FIG. 10.

The convolution kernels throughout the GAN were set to be 3×3. These kernels were randomly initialized by using a truncated normal distribution with a standard deviation of 0.05 and a mean of 0; all the network biases were initialized as 0. The learnable parameters are updated through the training stage of the deep neural network 10 by back propagation (illustrated in dashed arrows of FIG. 10) using an adaptive moment estimation (Adam) optimizer with learning rate $1\times10^{-4}$ for the generator network 70 and $1\times10^{-5}$ for the discriminator network 74. Also, for each iteration of the discriminator 74, there were 4 iterations of the generator network 70, to avoid training stagnation following a potential over-fit of the discriminator network to the labels. A batch size of 10 was used in the training.

Once all the fields-of-view have passed through the network 10, the whole slide images are stitched together using the Fiji Grid/Collection stitching plugin (see, e.g., Schindelin, J. et al. Fiji: an open-source platform for biological-image analysis. Nat. Methods 9, 676-682 (2012), which is incorporated herein by reference). This plugin calculates the exact overlap between each tile and linearly blends them into a single large image. Overall, the inference and stitching took ~5 minutes and 30 seconds, respectively, per cm² and can be substantially improved using hardware and software advancements. Before being shown to the pathologists, sections which are out of focus or have major aberrations (due to e.g., dust particles) in either the auto-fluorescence or bright-field images are cropped out. Finally, the images were exported to the Zoomify format (designed to enable viewing of large images using a standard web browser; http://zoomify.com/) and uploaded to the GIGAmacro website (https://viewer.gigamacro.com/) for easy access and viewing by the pathologists.

Implementation Details

The other implementation details, including the number of trained patches, the number of epochs and the training times are shown in Table 5 below. The digital/virtual staining deep neural network 10 was implemented using Python version 3.5.0. The GAN was implemented using TensorFlow framework version 1.4.0. Other python libraries used were os, time, tqdm, the Python Imaging Library (PIL), SciPy, glob, ops, sys, and numpy. The software was implemented on a desktop computer with a Core i7-7700K CPU @ 4.2 GHz (Intel) and 64 GB of RAM, running a Windows 10 operating system (Microsoft). The network training and testing were performed using dual GeForce® GTX 1080Ti GPUs (NVidia).

TABLE 5

| Virtual staining network | # of training patches | # of epochs | Training time (hours) |
| --- | --- | --- | --- |
| Salivary gland (H&E) | 2768 | 26 | 13.046 |
| Thyroid (H&E) | 8336 | 8 | 12.445 |
| Thyroid (H&E, transfer learning) | 8336 | 4 | 7.107 |
| Liver (Masson's Trichrome) | 3840 | 26 | 18.384 |
| Lung (Masson's Trichrome) | 9162 | 10 | 16.602 |
| Kidney (Jones stain) | 4905 | 8 | 7.16 |
| Liver (Masson's Trichrome, WSI) | 211475 | 3 | 39.64 |
| Kidney (Jones stain, WSI) | 59344 | 14 | 57.05 |
| Ovary 1 | 4738 | 84 | 37.21 |
| Ovary 2 | 11123 | 14 | 37.41 |
| Salivary Gland - 1 | 4417 | 65 | 24.61 |
| Salivary Gland - 2 | 2652 | 90 | 23.9 |
| Salivary Gland - 3 | 13262 | 24 | 30.58 |
| Breast | 67188 | 4 | 24.85 |
| Skin | 2566 | 124 | 27.02 |
| Skin (DAPI + CY5) | 2566 | 124 | 29.62 |
| Prostate | 677 | 472 | 30.27 |

While embodiments of the present invention have been shown and described, various modifications may be made without departing from the scope of the present invention. The invention, therefore, should not be limited, except to the following claims, and their equivalents.

What is claimed is:

1. A method of generating a digitally stained microscopic image of a label-free sample comprising:
    providing a trained, deep neural network that is executed by image processing software using one or more processors of a computing device, wherein the trained, deep neural network is trained with a plurality of matched chemically stained images or image patches and their corresponding fluorescence images or image patches of the same sample;
    obtaining one or more fluorescence images of the sample using a fluorescence microscope and one or more excitation light sources, wherein fluorescent light is emitted from endogenous fluorophores or other endogenous emitters of frequency-shifted light within the sample;
    inputting the one or more fluorescence images of the sample to the trained, deep neural network; and
    the trained, deep neural network outputting the digitally stained microscopic image of the sample that is substantially equivalent to a corresponding brightfield image of the same sample that has been chemically stained.

2. The method of claim 1, wherein the trained, deep neural network comprises a convolutional neural network.

3. The method of claim 1, wherein the deep neural network is trained using a Generative Adversarial Network (GAN) model.

4. The method of claim 1, wherein the sample is further labeled with one or more exogenous fluorescent labels or other exogenous emitters of light.

5. The method of claim 1, wherein the deep neural network is trained using a generator network configured to learn statistical transformation between the matched chemically stained and fluorescence images or image patches of the same sample and a discriminator network configured to discriminate between a ground truth chemically stained image of the sample and the outputted digitally stained microscopic image of the sample.

6. The method of claim 1, wherein the sample comprises mammalian tissue, plant tissue, cells, pathogens, biological fluid smears, or other objects of interest.

7. The method of claim 1, wherein the deep neural network is trained with samples of the same type as the sample type of the obtained one or more fluorescence image(s).

8. The method of claim 1, wherein the trained, deep neural network outputs a digitally stained microscopic image in less than one second of inputting the one or more fluorescence image(s).

9. The method of claim 1, wherein the sample comprises a non-fixed tissue sample.

10. The method of claim 1, wherein the sample comprises a fixed tissue sample.

11. The method of claim 10, wherein the fixed tissue sample is embedded in paraffin.

12. The method of claim 1, wherein the sample comprises a fresh tissue sample.

13. The method of claim 1, wherein the sample comprises tissue imaged in vivo.

14. The method of claim 1, wherein the excitation light source emits ultra-violet or near ultra-violet light.

15. The method of claim 1, wherein the one or more fluorescence images are obtained at a filtered emission band or emission wavelength range using one or more filters of a filter set.

16. The method of claim 15, wherein a plurality of filters are used to capture a plurality of fluorescence images which are input to the trained, deep neural network.

17. The method of claim 16, wherein the plurality of fluorescence images are obtained by multiple excitation light sources emitting light at different wavelengths or wavelength bands.

18. The method of claim 1, wherein the one or more fluorescence images is/are subject to one or more linear or non-linear image pre-processing operations selected from contrast enhancement, contrast reversal, image filtering prior to being input to the trained, deep neural network.

19. The method of claim 17, wherein the one or more fluorescence images and one or more pre-processed images are input together into the trained, deep neural network.

20. The method of claim 1, wherein the plurality of matched chemically stained and fluorescence images or image patches of the same sample are subject to registration during training, comprising a global registration process that corrects for rotation and a subsequent local registration process that matches local features found in the matched chemically stained and fluorescence images.

21. The method of claim 1, wherein the trained, deep neural network is trained using one or more GPUs or ASICs.

22. The method of claim 1, wherein the trained, deep neural network is executed using one or more GPUs or ASICs.

23. The method of claim 1, wherein the digitally stained microscopic image of the sample is output in real time or near real time after obtaining the one or more fluorescence images of the sample.

24. The method of claim 23, wherein the trained, deep neural network is trained for a second tissue/stain combination using initial neural network weights and biases from a first tissue/stain combination which are optimized for the second tissue/stain combination using transfer learning.

25. The method of claim 23, wherein the trained, deep neural network is trained for multiple tissue/stain combinations.

26. The method of claim 23, wherein the trained, deep neural network is trained for more than one chemical stain type for a given tissue type.

27. A method of generating a digitally stained microscopic image of a label-free sample comprising:
providing a trained, deep neural network that is executed by image processing software using one or more processors of a computing device, wherein the trained, deep neural network is trained with a plurality of matched chemically stained images or image patches and their corresponding fluorescence images or image patches of the same sample;
obtaining a first fluorescence image of the sample using a fluorescence microscope and wherein fluorescent light at a first wavelength or wavelength range is emitted from endogenous fluorophores or other endogenous emitters of frequency-shifted light within the sample;
obtaining a second fluorescence image of the sample using a fluorescence microscope and wherein fluorescent light at a second wavelength or wavelength range is emitted from endogenous fluorophores or other endogenous emitters of frequency-shifted light within the sample
inputting the first and second fluorescence images of the sample to the trained, deep neural network; and
the trained, deep neural network outputting the digitally stained microscopic image of the sample that is substantially equivalent to a corresponding brightfield image of the same sample that has been chemically stained.

28. The method of claim 27, wherein the first fluorescence image and the second fluorescence image are obtained using different resolutions.

29. The method of claim 27, wherein the sample comprises tissue, cells, pathogens, biological fluid smears, or other objects of interest.

30. A system for generating digitally stained microscopic images of a chemically unstained sample comprising:
a computing device having image processing software executed thereon or thereby, the image processing software comprising a trained, deep neural network that is executed using one or more processors of the computing device, wherein the trained, deep neural network is trained with a plurality of matched chemically stained images or image patches and their corresponding fluorescence images or image patches of the same sample, the image processing software configured to receive one or more fluorescence image(s) of the sample and output the digitally stained microscopic image of the sample that is substantially equivalent to a corresponding brightfield image of the same sample that has been chemically stained.

31. The system of claim 30, wherein the trained, deep neural network comprises a convolutional neural network.

32. The system of claim 31, wherein the trained, deep neural network is trained using a Generative Adversarial Network (GAN) model.

33. The system of claim 30, further comprising a fluorescent microscope configured to obtain the one or more fluorescence image(s) of the sample.

34. The system of claim 33, further comprising a plurality of filters wherein a plurality of fluorescence images are obtained using different filters.

35. The system of claim 33, wherein the fluorescent microscope comprises multiple excitation light sources emitting light at different wavelengths or wavelength bands.

36. The system of claim 32, wherein the GAN model is trained using a generator network configured to learn statistical transformation between the matched chemically stained and fluorescence images or image patches of the same sample and a discriminator network configured to discriminate between a ground truth chemically stained image of the same sample and the outputted digitally stained microscopic image of the sample.

37. The system of claim 32, wherein the GAN model is trained with a sample of the same sample type as the sample of the obtained one or more fluorescence image(s).

38. The system of claim 30, wherein the trained, deep neural network outputs a digitally stained microscopic image in less than one second of inputting the one or more fluorescence image(s).

39. The system of claim 30, wherein an excitation light source of the fluorescent microscope emits ultra-violet or near ultra-violet light.

40. The system of claim 33, wherein the one or more fluorescence image(s) is/are obtained at a filtered emission band or emission wavelength range using a filter set.

41. The system of claim 40, wherein the filter set comprises one of a plurality of filters configured for use with the fluorescence microscope.

* * * * *